United States Patent
Aljitawi et al.

(10) Patent No.: US 9,814,802 B2
(45) Date of Patent: Nov. 14, 2017

(54) METHOD FOR PROMOTING HAIR GROWTH COMPRISING IMPLANTING A TISSUE SCAFFOLD COMPRISING CK-19 POSITIVE CELLS DERIVED FROM WHARTON'S JELLY MESENCHYMAL STROMAL CELLS

(71) Applicants: The University of Kansas, Lawerence, KS (US); The Children's Mercy Hospital, Kansas City, MO (US)

(72) Inventors: Omar Aljitawi, Lawrence, KS (US); Richard Hopkins, Kansas City, KS (US); Michael Detamore, Lawrence, KS (US); Rama Garimella, Lawrence, KS (US)

(73) Assignees: The University of Kansas, Lawrence, KS (US); The Children's Mercy Hospital, Kansas City, MO (US)

( * ) Notice: Subject to any disclaimer, the term of this patent is extended or adjusted under 35 U.S.C. 154(b) by 158 days.

(21) Appl. No.: 13/874,054

(22) Filed: Apr. 30, 2013

(65) Prior Publication Data

US 2014/0148915 A1 May 29, 2014

Related U.S. Application Data

(60) Provisional application No. 61/687,715, filed on Apr. 30, 2012, provisional application No. 61/687,716, filed on Apr. 30, 2012.

(51) Int. Cl.
*A61L 27/36* (2006.01)
*A61L 27/38* (2006.01)

(52) U.S. Cl.
CPC ....... *A61L 27/3604* (2013.01); *A61L 27/3683* (2013.01); *A61L 27/3804* (2013.01); *A61L 2430/18* (2013.01)

(58) Field of Classification Search
CPC ............. A61L 2430/18; A61L 27/3604; A61L 27/3804; A61L 27/3683
See application file for complete search history.

(56) References Cited

U.S. PATENT DOCUMENTS

| | | | |
|---|---|---|---|
| 8,685,732 B2 * | 4/2014 | Font Perez et al. | 435/395 |
| 2004/0054410 A1 * | 3/2004 | Barrows | 623/15.11 |
| 2007/0212335 A1 * | 9/2007 | Hantash et al. | 424/93.7 |
| 2008/0069895 A1 * | 3/2008 | Liu et al. | 424/583 |
| 2008/0095748 A1 * | 4/2008 | Kharazi et al. | 424/93.7 |

FOREIGN PATENT DOCUMENTS

CN   102198292 A   9/2011

OTHER PUBLICATIONS

Yoo et al. "Application of mesenchymal stem cells derived from bone marrow and umbilical cord in human hair multiplication." J Dermatol Sci. Nov. 2010;60(2):74-83.*
Campard et al. "Native umbilical cord matrix stem cells express hepatic markers and differentiate into hepatocyte-like cells." Gastroenterology. Mar. 2008;134(3):833-48.*
"The Umbilical Cord." http://www.medicine.yale.edu/obgyn/kliman/Umbilical%20Cord%20EOR_tcm607-163162_tcm607-284-32.pdf. accessed Nov. 4, 2015.*
http://taxonomia.galeon.com/contenido/subclase.htm "Non Placental Mammals." accessed Jan. 4, 2017.*
Heino et al. "Comparison of the osteogenic capacity of minipig and human bone marrow-derived mesenchymal stem cells." J Orthop Res. Jul. 2012:30(7)1019-25.*
Barralet et al. "Tissue engineering of human biliary epithelial cells on polyglycolic acid/polycaprolactone scaffolds maintains long-term phenotypic stability." Tissue Eng. Oct. 2003;9(5):1037-45.*
Ribeiro eta l. Culture of equine bone marrow mononuclear fraction and adipose tissue-derived stromal vascular fraction cells in different media.Pesquisa Veterinária Brasileira. Dec. 2013; 33(Suppl. 1), 20-24.*
Baharvand et al. "Differentiation of human embryonic stem cells into hepatocytes in 2D and 3D culture systems in vitro." Int. J. Dev. Biol. 50: 645-652 (2006).*
Schwartz et al. "Multipotent adult progenitor cells from bone marrow differentiate into functional hepatocyte-like cells." J Clin Invest. May 2002;109(10):1291-302.*
Wu et al. "Effects of DMEM and RPMI 1640 on the biological behavior of dog periosteum-derived cells." Cytotechnology. Mar. 2009;59(2):103-11.*

* cited by examiner

*Primary Examiner* — Titilayo Moloye
(74) *Attorney, Agent, or Firm* — Maschoff Brennan

(57) ABSTRACT

A method of differentiating cells into CK19-positive cells capable of producing hair follicle-like and hair structure-like can include: providing a tissue scaffold; seeding cells into the scaffold, the cells being capable of differentiation; incubating the scaffold having the cells in a cell growth media; and incubating the scaffold having the cells in an osteogenic differentiation medium sufficient for CK19-positive cells to be generated in the scaffold. The tissue scaffold can be a decellularized Whartons' jelly matrix. The cell growth media excludes osteogenic differentiation components: dexamethasone, β-glycerophosphate, 1α,25-hydroxyvitamin D3, and ascorbic acid 2-phosphate. The osteogenic differentiation medium includes the osteogenic differentiation components. The cells can be mesenchymal cells, such as WJMSCs.

19 Claims, 24 Drawing Sheets

METHOD FOR PROMOTING HAIR GROWTH COMPRISING IMPLANTING A TISSUE SCAFFOLD COMPRISING CK-19 POSITIVE CELLS DERIVED FROM WHARTON'S JELLY MESENCHYMAL STROMAL CELLS

CROSS-REFERENCE TO RELATED APPLICATIONS

This patent application claims priority to U.S. Provisional Application No. 61/687,715 filed Apr. 30, 2012 and to U.S. Provisional Application No. 61/687,716 filed Apr. 30, 2012, which provisional applications are incorporated herein by specific reference in their entirety.

BACKGROUND

Mesenchymal stem cells (MSCs), which are sometimes referred to as marrow stromal cells or mesenchymal stromal cells, are multipotent stromal cells that can differentiate into a variety of cell types, including: osteoblasts (bone cells), chondrocytes (cartilage cells), and adipocytes (fat cells). This phenomenon has been documented in specific cells and tissues in living animals and their counterparts growing in tissue culture. Mesenchyme is embryonic connective tissue that is derived from the mesoderm and that differentiates into hematopoietic and connective tissue, whereas MSCs do not differentiate into hematopoietic cells. Stromal cells are connective tissue cells that form the supportive structure in which the functional cells of the tissue reside. While this is an accurate description for one function of MSCs, the term fails to convey the relatively recently-discovered roles of MSCs in the repair of tissue. Because the cells, called MSCs by many labs today, can encompass multipotent cells derived from other non-marrow tissues, such as umbilical cord blood, adipose tissue, adult muscle, corneal stroma or the dental pulp of deciduous baby teeth, yet do not have the capacity to reconstitute an entire organ, the term "Multipotent Stromal Cell" has been proposed as a better replacement for the abbreviation for stem cells that can differentiate into various types of tissues.

The youngest, most primitive MSCs can be obtained from the umbilical cord tissue, namely Wharton's jelly and the umbilical cord blood. However the MSCs are found in much higher concentration in the Wharton's jelly compared to the umbilical cord blood, which is a rich source of hematopoietic stem cells. The umbilical cord is easily obtained after the birth of the newborn, is normally thrown away and poses no risk for collection. The umbilical cord MSCs have more primitive properties than other adult MSCs obtained later in life, which might make them a useful source of MSCs for clinical applications. The advances in biotechnology have recognized the importance of promoting differentiation into desired types of cells and tissues.

Therefore, it can be advantageous to develop new compositions and techniques for promoting differentiation of MSCs into desired types of cells and tissues.

SUMMARY

In one embodiment, a method of differentiating cells into CK19-positive cells can include: providing a tissue scaffold; seeding cells into the scaffold, the cells being capable of differentiation; incubating the scaffold having the cells in a cell growth media; and incubating the scaffold having the cells in an osteogenic differentiation medium sufficient for CK19-positive cells to be generated in the scaffold. In one aspect, the tissue scaffold is a decellularized Whartons' jelly matrix. In one aspect, the cell growth media excludes osteogenic differentiation components: dexamethasone, β-glycerophosphate, 1α,25-hydroxyvitamin D3, and ascorbic acid 2-phosphate. In one aspect, the osteogenic differentiation medium includes the osteogenic differentiation components. In one aspect, the cells are selected from the group consisting of smooth muscle cells, fibroblasts, chondrocytes, prechondrocytes, endothelial cells, dendritic cells, keratinocytes, myogenic cells, stem cells, muscle cells, epithelial cells, mesenchymal cells, and combinations thereof. In one aspect, the cells are mesenchymal cells, such as WJMSCs. In one aspect, the method can include incubating the scaffold having the cells until a region thereof until one or more of versican, sonic hedgehog, and/or bone morphogenic protein-4 (BMP-4) is detected. In one aspect, the method can include incubating the scaffold having the cells until an area of condensed cells forms with one or more layers of spindle-like cells over the area of condensed cells. In one aspect, the method can include incubating the scaffold having the cells until a placode is formed. In one aspect, the method can include incubating the scaffold having the cells until a hair follicle-like structure is formed. In one aspect, the method can include incubating the scaffold having the cells until an osteogenic portion is obtained.

In one embodiment, a method of promoting hair growth can include: providing a tissue scaffold having Wharton's jelly matrix with CK19-positive cells; and implanting the tissue scaffold in skin of a subject. In one aspect, the method can include implanting the tissue scaffold into a scalp of a subject. In one aspect, the scaffold includes a region thereof having more of versican, sonic hedgehog, and/or bone morphogenic protein-4 (BMP-4) being detectable. In one aspect, the scaffold includes a region having an area of condensed cells with one or more layers of spindle-like cells over the area of condensed cells. In one aspect, the scaffold includes a placode.

In one embodiment, a method of generating spheroids having CK19-positive cells can include: providing cells capable of differentiating; incubating the cells in an expansion medium; and incubating the cells in an osteogenic differentiation medium sufficient for formation of spheroids having CK19-positive cells. In one aspect, the cell growth media excludes osteogenic differentiation components and the osteogenic differentiation medium includes osteogenic differentiation components, the osteogenic differentiation components including: dexamethasone, β-glycerophosphate, 1α,25-hydroxyvitamin D3, and ascorbic acid 2-phosphate. In one aspect, the cells are selected from the group consisting of smooth muscle cells, fibroblasts, chondrocytes, prechondrocytes, endothelial cells, dendritic cells, keratinocytes, myogenic cells, stem cells, muscle cells, epithelial cells, mesenchymal cells, and combinations thereof. In one aspect, the cells are mesenchymal cells, such as WJMSCs. In one aspect, the method can include incubating the cells until: a region forms with one or more of versican, sonic hedgehog, and/or bone morphogenic protein-4 (BMP-4) being detectable; until an area of condensed cells forms with one or more layers of spindle-like cells over the area of condensed cells; until a placode is formed; and/or until a hair follicle-like structure is formed.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings:

DETAILED DESCRIPTION

Figure 1A:
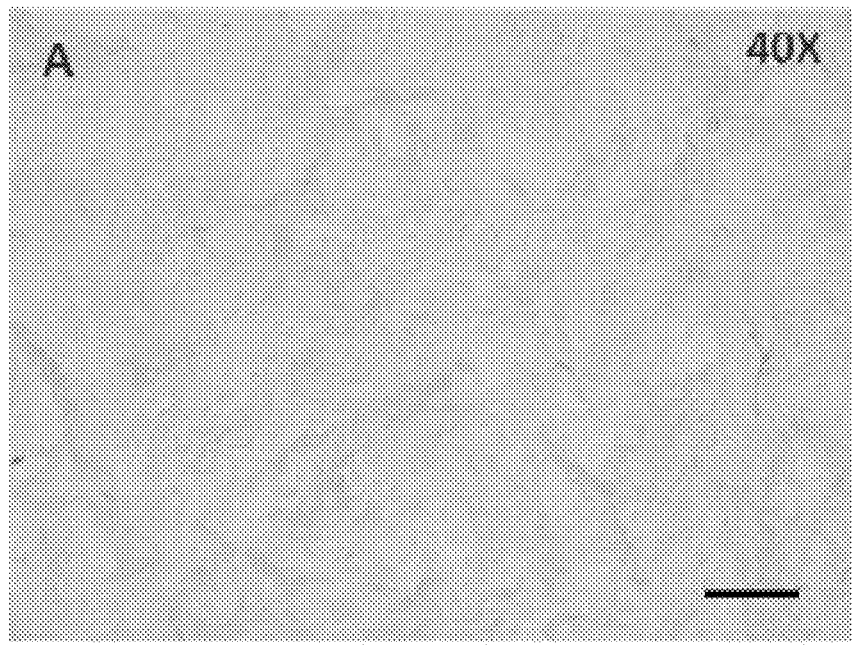
FIG. 1A includes an image of DWJM devoid of cellular elements.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Wharton's jelly mesenchymal stromal cells (WJMSCs) are considered mesenchymal cells as defined by the International Society for Cellular Therapy (Troyer D L, Weiss M L. Wharton's jelly-derived cells are a primitive stromal cell population. Stem Cells 2008; 26:591-9). Accordingly, they are multipotent cells capable of differentiating into adipose, bone, cartilage, muscle, and neural cells, which are generally known in the art. With the exception of neural cells these tissues are mesodermal in origin. Since differentiation into cells of all somatic lineages is a feature of pluripotent stem cells like embryonic stem cells, (Yu J, Thomson J A. Pluripotent stem cell lines. Genes & development 2008; 22:1987-97), differentiation of mesenchymal stromal cells into cells of mesodermal or ectodermal origin raises the question of whether mesenchymal stromal cells are pluripotent.

Additionally, hair follicle development and morphogenesis is largely regulated through epithelial-mesenchymal interactions that occur during embryonic development and continue to occur during adult life (Fuchs E. Scratching the surface of skin development. Nature 2007; 445:834-42). Several pathways govern these interactions and these include: sonic hedgehog (shh) and bone morphogenic proteins (Woo W M, Zhen H H, Oro A E. Shh maintains dermal papilla identity and hair morphogenesis via a Noggin-Shh regulatory loop. Genes & development 2012; 26:1235-46; Plikus M V, Mayer J A, de la Cruz D, et al. Cyclic dermal BMP signalling regulates stem cell activation during hair regeneration. Nature 2008; 451:340-4).

Generally, the present invention includes cell culture systems and methods for inducing mesenchymal cells to differentiate into CK19-positive cells. The mesenchymal cells can be induced to differentiate and develop into hair-growing structures or tissues, which include the CK19-positive cells. In one aspect, the mesenchymal can be Wharton's jelly mesenchymal stromal cells (WJMSCs), which now can be induced to form CK19-positive cells in tissues with cell-layering that allows for growing hair from the tissues in vitro. It is expected that the systems and methods may be useful for differentiating mesenchymal CK19-positive cells and forming hair-growing tissues in vivo. It is also expected that the CK19-positive cells and hair-growing tissues can be manipulated and implanted to a subject for growing hair on the subject. It is also expected that the CK19-positive cells and tissues having the same can be prepared into hair follicle cells that grow hair. It appears that the tissue stratification and layering with CK19-positive cells may be differentiating into follicle cells that can be used for growing hair structures, which is consistent with ectodermal differentiation.

The present invention can provide at least two distinct methodologies to generate the CK19-positive cells and tissues having the same that can be used to promote hair growth therefrom. The first methodology can include seeding WJMSCs on a matrix material isolated from decellularized Wharton's jelly matrix (DWJM), introducing the cells to an expansion medium, and then introducing the cells to a differentiation medium to promote differentiation into CK19-positive cells and tissues having the same that are capable of growing hair therefrom. In one aspect, the differentiation medium is not previously associated with promoting differentiation to CK19-positive cells or hair-growing tissue. In one aspect, the differentiation medium includes an osteogenic differentiation medium that has now been surprising and unexpectedly caused WJMSCs in a DWJM to differentiate into CK19 positive cells and tissue stratification that causes hair growth therefrom. In the other method, the WJMSCs were cultured without the DWJM in ordinary culture to form spheroids by using the same osteogenic media. The osteogenic media was also shown to induce WJMSCs to undergo osteogenic differentiation to form bone along with the formation of the CK19-positive cells and hair-growing tissue. As such, the present invention can utilize mesenchymal bone differentiation conditions to drive ectodermal differentiation, and to drive differentiation into CK19-positive cells and hair-growing tissue.

Accordingly, the mesenchymal cells can be grown on tissue engineering scaffolds prepared by decellularization of a tissue. "Decellularization", for purposes of the present invention, refers to the process of removing cells and/or cellular debris from a tissue. In a preferred embodiment the decellularization process prepares a tissue so as to be available to accept new cells into its biological scaffold. Accordingly, the decellularized tissue scaffolds can be prepared by any process of decellularization, such as the process described herein.

In one embodiment, the present invention can include a differentiation protocol that generates CK19-positive cells and tissue growing hair-like structures using WJMSCs seeded on DWJM subjected to osteogenic differentiation media in order to induce the WJMCs to differentiate into CK19-positive cells and tissue growing hair-like structures. The differentiation protocol can be performed so that CK19-positive cells become arranged into two distinct patterns after they are seeded on DWJM and introduced to the osteogenic differentiation media. The differentiation protocol can induce the cells to differentiate into a first pattern, where the differentiated cells appear spindle-like and surrounded the entirety of the surface of DWJM. The differentiation protocol can induce the cells to differentiation into a second pattern, where the differentiated cells appear cuboidal and occupy a region between the surface CK19 cells and an internal tissue region having a collagen I rich core of the DWJM. In the second pattern, the cells can be condensed into a discrete area that is similar to the phenomenon of dermal condensation of specialized mesenchymal cells that leads to formation of dermal papilla. These two patterns can be achieved in the same cell culture with the same differentiation protocol.

A recent study suggested that versican, an aggregating chondroitin sulfate proteoglycan, localizes to dermal papilla cells that have hair-induction abilities (Kishimoto J, Ehama R, Wu L, Jiang S, Jiang N, Burgeson R E. Selective activation of the versican promoter by epithelial-mesenchymal interactions during hair follicle development. Proceedings of the National Academy of Sciences of the United States of America 1999; 96:7336-41). Now, based on data described herein, the present invention can be used to induce mesenchymal cells to produce an equivalent of cell condensation and hair placode, such that the cell condensation area can express versican.

Additionally, sonic hedgehog (shh) signaling has recently been found to be essential for hair follicle development and morphogenesis (Mundy G, Gutierrez G, Garrett R, et al. Proteasome inhibitors stimulate both bone formation and hair growth by similar mechanisms. Annals of the New York Academy of Sciences 2007; 1117:298-301; Chiang C, Swan R Z, Grachtchouk M, et al. Essential role for Sonic hedgehog during hair follicle morphogenesis. Developmental biology 1999; 205:1-9) but not necessarily for follicle initiation (St-Jacques B, Dassule H R, Karavanova I, et al. Sonic hedgehog signaling is essential for hair development. Current biology: CB 1998; 8:1058-68). The shh signaling has also been reported to be expressed by epithelial cells in the hair follicle (Motoyama J, Takabatake T, Takeshima K, Hui C. Ptch2, a second mouse Patched gene is co-expressed with Sonic hedgehog. Nature genetics 1998; 18:104-6). Now, based on data described herein, the present invention can be used to induce mesenchymal cells to produce shh in the cell condensation area.

Also, bone morphogenic protein-4 (BMP-4) was recently found to be produced in a cyclic fashion by the dermis and as a result regulate the growth of hair follicles (Plikus M V, Mayer J A, de la Cruz D, et al. Cyclic dermal BMP signalling regulates stem cell activation during hair regeneration. Nature 2008; 451:340-4). According to Plikus et al, BMP-4 expression was low in early anagen phase (propagating anagen) and high in late anagen phase (autonomous anagen). Now, based on data described herein, the present invention can be used to induce mesenchymal cells to produce BMP-4 expression and to allow hair structure development. The BMP-4 expression can be low, but detectable. The detectable or secreted BMP-4 may diminish over time as the CK19-positive cells and scaffold having the same are transformed toward being capable of growing hair.

The present invention can induce mesenchymal differentiation and cause epithelial-mesenchymal interactions. Versican localization in dermal condensation can be detected as a part of a determination or detection of the presence of epithelial-mesenchymal interactions that can be present from CK19-positive cells and tissues having the same that can grow hair or hair-like structures. Also, showing BMP-4 and shh expression from differentiation from mesenchymal cells can be used to establish that hair-growing tissue can be obtained from mesenchymal cells. As such, the present invention can be used to exploit the underlying mechanisms of hair morphogenesis, to enhance the process of in vitro hair development, and to develop and optimize bioengineered hair follicle structures for hair transplantation as well as in vivo applications and de novo hair growth from the cells and tissues described herein.

The CK19-positive cells and tissues growing hair-like structures can be used for assays for screening for substances that promote differentiation of mesenchymal cells into CK19-positive cells and tissues growing hair-like structures, or they can be used to screen for substances that inhibit the formation thereof. The assay cell culture having CK19-positive cells can be tested before, during or after exposure to screened substances for upregulation or downregulation in the cells or tissue of: versican expression; bone morphogenic protein-4 (BMP-4); and/or sonic hedgehog (shh). Here, upregulation may indicate that a substance promotes formation of CK19-positive cells and tissue growing hair-like structures (e.g., hair follicle development) from mesenchymal cells, and downregulation can indicate a substances that inhibits or stops formation of CK19-positive cells and tissue growing hair-like structures (e.g., hair follicle development). Substances that promote upregulation may be used in hair growth or regenerative therapies, while inhibitory substances may be useful in therapies or cosmetics to reduce or stop hair growth. For example, baldness may be treated with the substances that promote upregulation and formation of CK19-positive cells and tissue growing hair-like structures (e.g., hair follicle development). Such upregulators may be used in combination with the CK19-positive cells and tissue growing hair-like structures or hair follicles obtained from mesenchymal cells in hair growth promoting therapies. On the other hand, overly hair regions may be treated to reduce hair growth by the substances that promote downregulation. The substance screening protocols can include WJMSCs being seeded on DWJM with osteogenic differentiation media. The substances can be introduced to the mesenchymal cells before, during or after exposure to the osteogenic differentiation media. Supernatant can be collected at any time point, such as weekly, during culture and analyzed for BMP-4, shh and versican. Also, seeded DWJM pieces can be harvested, fixed, and stained for BMP-4, shh and/or versican. Isolated protein, extracted from DWJM pieces, can also be used for BMP-4 and versican Western blots in order to identify upregulators and downregulators thereof.

In addition to screening for upregulators and downregulators, these protocols can be followed for developing and identifying CK19-positive cells and tissue growing hair-like structures or hair follicles obtained from mesenchymal cells, which can be used for hair-growth promoting therapies. Cells or tissues suitable for use in hair-growth promoting therapies can include production or upregulation of versican expression, bone morphogenic protein-4 (BMP-4), and/or sonic hedgehog (shh).

In one embodiment, BMP-4 expression may be weak, and thereby detection or assaying for the presence or upregulation thereof may be omitted in the protocols described herein. The secretion of BMP-4 may also decrease over time.

The cell culture systems and protocols can be used to promote mesenchymal cells to differentiate so as to develop an area of cell condensation. Such development of an area of cell condensation can be identified by expression or upregulation of versican and/or shh, or strong expression thereof. The area of cell condensation can be characterized as a placode, such as a hair placode. Visual or other identification thereof can be used.

Also, the cell culture systems and protocols can be used to promote mesenchymal cells to differentiate so as to form one or more layers of spindle-like cells over an area of cell condensation. The spindle-like cells can lie over the area of cell condensation. The spindle-like cells can lie over a hair placode. The spindle-like cells, often in multiple layers, can be identified by BMP-4 expression or upregulation. The spindle-like cells can be on a surface of the cell culture or tissue culture. For example, the surface layers of spindle-like cells can be detected by faintly expressed BMP-4 that is identified by immunohistochemistry. For example, BMP-4 expression can be measured by ELISA in supernatants, which expression amount can decrease over time as the culture grows. Also, BMP-4 and versican variants from the placode can be detected by Western blot to characterize the placode with spindle-like cell layers thereover.

The identification and characterization of the cell condensation into a placode and spindle-like cell layers over the placode can be used to determine cells or tissue that can be used for hair-growth therapies. The cell culture conditions described herein resulted in mesenchymal cells to differentiate to obtain cell condensation area at the interface of DWJM and seeded WJMCSs. The versican and shh expression, as well as changes in BMP-4 secretion, can be used to support the development of CK19-positive cells, cell cultures thereof, tissues thereof, and hair-like structures that can be used as described herein for screening or therapies.

The mesenchymal cells can be grown on a tissue scaffold. The tissue scaffold can be any type of tissue scaffold prepared from synthetic or natural materials ranging from polymer scaffolds, microsphere scaffolds, or the like. The mesenchymal cells may also be grown on scaffolds prepared by decellularizing tissues to form tissue scaffolds having spaces for cell growth. The spaces can be where cells were removed during decellularization. The decellularized tissue scaffolds can be obtained ready to use or prepared from a cellularized tissue. The cellularized tissue can be decellularized into a decellularized tissue scaffold, which can be referred to as a matrix having interstitial spaces sufficient for cell growth and propagation and differentiation.

In one embodiment, the present invention can provide a method of preparing a decellularized matrix. The decellularized matrix can be sufficiently prepared so that at least one cell type may be seeded thereon for cell growth and propagation and differentiation. The cell can be grown on the decellularized matrix in order to remodel the decellularized tissue into a useful tissue that can be used in assays or therapies. The remodeled tissue may also be used an implant, which includes the decellularized tissue with at least one cell type growing thereon. The method of preparing the decellularized tissue can include: providing at least a portion of an umbilical cord; isolating the umbilical cord matrix of the umbilical cord; and decellularizing the umbilical cord matrix. The decellularizing can be by any decellularizing protocol, such as the protocol described herein. In aspect, the decellularized umbilical cord matrix is Wharton's Jelly Matrix, which can be referred to as DWJM.

In one embodiment, the present invention can provide a method of differentiating a cell. The cell differentiation method can be used to prepare a differentiated tissue. The cell differentiation method can be used with any type of tissue scaffold; however, decellularized umbilical matrix can be preferred. As such, the cell differentiation method can include: seeding at least one cell type on the decellularized umbilical matrix; expanding the cell population with a cell growth medium; and immersing the seeded cell type in a differentiation medium to induce differentiation to a desired cell type. The cell growth medium is different from the differentiation medium. The cell growth medium can be a standard cell culture medium that is not configured or known to differentiate cells. The cell growth medium can be a typical cell culture expansion medium or other medium for cell growth that is not known or configured to induce cell differentiation. For example, the cell growth medium can be Dulbecco's Modified Eagle Medium (DMEM) with 10% fetal bovine serum (FBS) and 1% penicillin and streptomycin (Pen/strep). In one aspect, the umbilical cord matrix is Wharton's Jelly Matrix. The seeded cell type can be selected from the group consisting of smooth muscle cells, fibroblasts, chondrocytes, prechondrocytes, endothelial cells, dendritic cells, keratinocytes, myogenic cells, stem cells, muscle cells, epithelial cells, mesenchymal cells, WJMSCs, and combinations thereof. Preferably, the seeded stem cells are mesenchymal cells. Preferably, the decellularized umbilical matrix is DWJM. In one aspect, the differentiation medium is osteogenic differentiation media, such as the osteogenic differentiation media described herein or any cell culture media supplemented with the supplemental components described herein. The osteogenic differentiation media can be low-glucose DMEM supplemented by supplemental components 100 nM dexamethasone (DEX), 5 mM B-glycerophosphate (β-GP), 10 nM 1α,25-hydroxyvitamin D3 (VD3) and 50 μg/mL ascorbic acid 2-phosphate (AA2P). Also, the supplemental components can be included in a different media, such as another low-glucose media.

The cell differentiation protocol can result in the desired cell type including CK19-positive cells. A tissue can be obtained that has the CK19-positive cells in the decellularized umbilical matrix. The tissue can include the condensed cell areas or placode and spindle-like cells, and may have a hair follicle or pre-follicle. The CK19-positive cells can be indicative of the formation of hair follicle cells. Thus, the cell differentiation protocol can be used for the formation of CK19-positive cells, placode and spindle-like cell layers, hair follicles, or precursors therefor, which can be used in assays or therapies as described herein. The CK19-positive cells, placode and spindle-like cell layers, hair follicles, or precursors therefor can be removed from the culture and propagated separately. The CK19-positive cells, placode and spindle-like cell layers, hair follicles, or precursors therefor may be removed from the umbilical matrix and cast into a new cell culture. The CK19-positive cells, placode and spindle-like cell layers, hair follicles, or precursors therefor may be removed and implanted into an animal, such as a human. The implantation can be into the skin in associated or simulation of hair follicles. This may be useful in a method for treating baldness or promoting hair growth.

In one embodiment, the present invention can include a method of treating baldness or promoting hair growth. The methods can include applying to the skin (e.g., scalp) of an animal (e.g., mammal), a biomaterial containing CK19-positive cells. The CK19-positive cells can be obtained as described herein, such as by being derived from seeding mesenchymal cells (e.g., WJMSC) and growing the same on a decellularized matrix, such as a DWJM. In one aspect, the method can include obtaining CK19-positive cells, placode and spindle-like cell layers, hair follicles, or precursors therefor as described herein, and then implanting or otherwise growing the same on an area of skin that commonly has hair, such as the scalp. The growing can result in hair growth. This can also result in hair follicle formation or growth in the skin from the implanted biomaterial. While the methodology may be useful for any animal, it can be useful for a mammal that grows hair, such as a human. The location of hair growth that receives the biomaterial can be the scalp for hair growth on the head, face for beard for masculine hair growth, armpit, chest, back, genitals, legs, arms, or any other location. The implantation of the biomaterial can be by methods established in the art for skin or hair follicle implantation.

In one embodiment, a method can be performed for generating spheroid bodies. The spheroid bodies can include CK19-positive cells. As such, the spheroids can be used in the assays or treatments as described herein. The spheroid generating protocol can include: isolating WJMSC from the umbilical cord; expanding the WJMSC with growth medium; and culturing WJMSCs in differentiation medium. The growth medium and differentiation medium can each be prepared as described herein. As such, the growth medium can be a standard cell culture medium or growth medium, while the differentiation medium can be an osteogenic differentiation medium or have the osteogenic differentiation medium supplements. The spheroids can be characterized as having CK19-positive cells or hair follicle cells. The spheroids may be grown into hair follicles. The CK19-positive cells can be arranged diffusely about the spheroids. For example, a method of treating baldness or promoting hair growth can include obtaining the spheroid bodies having the CK19-positive cells, and applying the spheroid bodies to skin. The application can be implantation.

The growth of the spheroids was observed. In some areas of spheroids, the cells were close to forming hair-growing structures, where CK19-positive cells may indicate hair follicle cells. These cells appear to be arranged in structures that resemble hair follicle structures with cellular areas on the outside and a central clear area.

Experiments were conducted to analyze the ability to grow hair with respect to the spheroids and DWJM methodologies. It was found the hair structures were localized in close proximity to areas of calcification and mineralization evident by alizarin red stain in spheroids and to areas of bone matrix in DWJM. Accordingly, the methodology with DWJM can be used to generate both bone in one location of the DWJM member and hair in another location. Additionally, in the spheroids and DWJM, the areas of hair-like structures each appeared to have developed an area of invagination into the generated spheroid or DWJM. The areas of invagination and hair formation occurred at the epithelial (CK19-positive cells)-mesenchymal (bone matrix) junction in DWJM. Accordingly, the DWJM can provide an epithelial-mesenchymal interface to promote hair growth as described herein. This epithelial-mesenchymal interaction may be useful for morphogenesis of various organs, including hair follicles. These findings indicate that MSCs from umbilical cord tissue can be used generate hair. The CK19-positive cells were arranged in what appears to be a hair follicle closely associated with hair. To generate these cells, osteogenic differentiation medium was introduced to the mesenchymal cells.

In one embodiment, the DWJM can be seeded with mesenchymal cells and differentiated with osteogenic differentiation medium so that the distribution of CK19-positive cells is on one side of the outside of DWJM in a concentrated manor, while the bone matrix occupied the inner side of DWJM, which resembles what happens during embryogenesis at the blastocyst stage. In blastocysts, the outer layer represents the ectodermal layer and the middle layer represents the mesodermal layer. In the present invention, CK19-positive cells represent cells of ectodermal differentiation, while the bone matrix represents a mesodermal structure in the DWJM. Additionally, the blastocyst structure is polarized where the inner cell mass occupies one side of the blastocyst. Similarly, in DWJM, CK19-positive cells were concentrated in one area, besides the outer layer of the DWJM. These findings indicate that some embryonic characteristics are being dictated by using an embryonic tissue like DWJM.

In one embodiment, the DWJM can be seeded with MSCs and differentiated so as to form dermal papilla-like tissue (DPLT) using the osteogenic differentiation medium and the protocols described herein. In one aspect, dermal papilla forming medium is specifically not used. The osteogenic differentiation medium when used as described herein can generate CK19-positive cells arranged in what appears to be a hair follicle closely associated with hair. This procedure generated both osteogenic differentiated cells and CK19-positive hair follicle cells.

Experiments were conducted on the in vitro model described herein in order for hair follicle development to occur in vitro, which mimics the in vivo hair follicle development during embryogenesis. Additionally, the experiments were performed with one cell source that provided the epithelial and the mesenchymal components of hair follicle. These cells were isolated from Wharton's jelly, which then orientated themselves in the DWJM in a way that led to creating an epithelial-mesenchymal equivalent interaction that led to hair formation. The cell condensation area in our model developed when WJMSCs interacted with DWJM. This interaction later resulted in the formation of a surface layer of spindle cells that surrounds DWJM and an area where WJMSCs form cell condensation. This cell condensation area was morphologically distinct from the surface area as the cells are cuboidal and not spindle-like cells and was rich in matrix material. Additionally, this area was rich in extracellular matrix material and strongly expressed versican and shh. This structural development resembled the epidermal-mesenchymal interaction for hair follicle development. The model clearly demonstrated very prominent versican expression in the cell condensation area. Versican, given this role in cell proliferation, might have led to the noticed changes in the shape of the cells within the cell condensation area and in the overlying cells in the model.

Normally, during hair follicle development, cells in the area of mesenchymal condensation interact with the overlying epithelial cells and induce epithelial thickness and hair placode formation. In our model, versican positive spindle-like cells formed multiple layers (see FIGS. 8A, 8B and 8C) overlying the area of cell condensation while they formed a single layer around the rest of DWJM (see FIG. 8A). These multilayered versican positive spindle-like cells potentially correspond to hair placode (see FIG. 8C).

The model demonstrated that the area of cell condensation had invaded into the matrix core forming tubular structures. The DWJM core was found to be highly rich in collagen I. The collagen I rich core DWJM core may provide the cells in the cell condensation area with a signal to invade the core by forming tubular structures.

Sonic Hedgehog (shh) is one of the regulators of hair follicle development that is produced by the mesenchymal dermal papillae and drives the development of the overlying epithelial layer. In our model, the area of cell condensation significantly expressed shh. Adjacent to the area of cell condensation, cuboidal cells with cell processes exhibited shh positivity. This area next to cell condensation area might be potentially considered the equivalent of dermal papillae cells that drive the morphogenesis of overlying spindle-like surface cell layers. Accordingly, the protocols of the invention can lead to substantial formation of dermal papilla.

On the other hand, BMPs including BMP-4 produced by the dermal papillae have been described to provide a cyclic signal to the overlying hair follicle stem cells during hair development. The model demonstrated BMP-4 expression by Western blot, and demonstrated its localization to the area of cell condensation and the overlying spindle-like cells. However, BMP-4 secretion decreased overtime during the 4-5 week in vitro culture in DWJM. Collectively, the results indicate that BMP-4 continued to be produced by the epithelial-mesenchymal equivalent areas, but its release might have been inhibited at the end of the 4 week culture due to overlaying spindle-like cell layers. Since BMP signaling is found to inhibit epithelial stem cell activity, it is conceptualized that it had to be inhibited in our model to allow the hair follicle to develop. The model demonstrated an increase in CK19 expression, determined by western blot, over time during osteogenic differentiation. Since CK19 is an epithelial cell marker, it is speculated that the decrease in secreted BMP-4 during osteogenic differentiation cultures was associated with an increase in epithelial stem cell activity.

In one embodiment, the differentiated cells and tissues having the same described herein can be used for bioengineering hair follicles, which can be transplanted. The model provides a delivery method that provides the main components of hair follicle, and even rudimentary hair follicle with hair structures. These can be implanted and developed further into hair follicle and growing hair.

In one embodiment, the DWJM matrix can be used to support the growth and osteogenic and chondrogenic differentiation of MSCs based on histology, electron microscopy, and gene expression studies and the osteogenic differentiation of MC3T3E1, a murine osteoblastic cell line. That is, besides hair growth, the DWJM can be used for osteogenic and chondrogenic differentiation. The DWJM can be used to support various populations of cells, including undifferentiated mesenchymal cells. Biochemically, DWJM is rich in collagen and hyaluronan and contains sulfated glycosaminoglycan. Hyaluronan widely expresses the archetypal hyaluronan receptor, CD44, is also expressed on osteocytes, chondrocytes, and hematopoietic marrow cells. This allows for hyaluronan to link with chondrocytes in cartilage and with osteocytes and osteoclasts in bone, an interaction felt to be important for maintaining cartilage and bone homeostasis. Since MSCs express CD44, this interaction also explains their attachment to matrix. Additionally, successful tissue engineering requires growth factors to support growth and differentiation of transplanted cells. Interestingly, DWJM is also a rich source of peptide growth factors, notably insulin like growth factor-1 (IGF-1) and to a lesser extent platelet derived growth factor (PDGF), which are both linked to controlling cell proliferation, differentiation and synthesis and remodeling of the extracellular matrix. Finally, high molecular weight hyaluronan was also found to be osteoinductive in some in vivo studies, which supports its role as a scaffold for bone tissue engineering.

MC3T3E1, a murine osteoblast cell line, was used to demonstrate that other cells lines can be seeded and differentiated using DWJM. Successful DWJM decellularization was achieved and verified by histology, electron microscopy and DNA quantification in the resulting DWJM. A decellularized scaffold devoid of cells with an average dsDNA removal of 96.6% (+1-0.4%) was successfully obtained. Mass spectrometry analysis identified several proteins, including collagen, fibronectin I, tenascin and lumican. DWJM also contained an average of 0.661(+/−0.09) µg/mg sulfated GAGs. Subsequent DWJM cell seeding followed by osteogenic and chondrogenic differentiation was verified by histology, electron microscopy, and molecular tests, as described herein. Following 6 weeks of osteogenic differentiation, collagen I, runt-related transcription factor 2, and osteocalcin genes were significantly expressed over their respective control values. Similarly, aggrecan gene expression was significantly expressed over its respective control value after 6 weeks of chondrogenic differentiation.

Experiments demonstrated a clear attraction between undifferentiated MSCs and the DWJM, which may result in successful seeding of the WJMSCs into the DWJM. The data also demonstrates attraction of MC3T3E1 cell line to DWJM and attachment within minutes. Despite the attraction between WJMSCs and DWJM, some areas of the DWJM were not as attractive as others, which lead to differences in seeding efficiency in different parts of DWJM. This was noted earlier when WJMSCs variably seeded the different parts of DWJM, and was noted later on examination of histology sections of the seeded DWJM. It is believed the difference in seeding efficiencies is related to the different tissue surface orientations identified on SEM pictures. For example, one surface of the matrix is made of compact tissue with no lacunae available for cells to penetrate, while others have surfaces with large-sized and intermediate-sized lacunae, which allow the cells to penetrate DWJM. These surfaces result from WJ orientation in umbilical cords and as a result of the blinded decellularization process.

The data demonstrated evidence of osteogenic differentiation based on histology and expression of genetic markers of differentiation like runx 2. The runx 2 expression, an early marker of osteogenic differentiation, was not significantly increased until week 4 of differentiation, while OCN, a later marker of osteogenic differentiation, was not detected during the 4 weeks of osteogenic differentiation. Together, these findings make us believe that WJMSCs underwent early stages of osteogenic differentiation when seeded onto DWJM and subjected to osteogenic differentiation medium for 4 weeks. Interestingly, col I expression decreased overtime after osteogenic differentiation compared to col I expression in undifferentiated MSCs. It was noticed that col I expression reciprocally correlated with the changes in runx 2 expression.

Chondrogenic differentiation was also demonstrated based on histology and expression of SOX-9. Interestingly, two weeks following chondrogenic differentiation, SOX-9 expression significantly declined from pre-chondrogenic induction levels. In the subsequent two weeks, SOX-9 showed significant increase from the low levels at week 2 of chondrogenic differentiation, which is expected in response to chondrogenic differentiation. Other chondrogenic differentiation markers, like col II and aggrecan were not detected in experiments. This could be because the chondrogenic differentiation seemed to occur 4 weeks post chondrogenic differentiation evident by increase in SOX-9 expression.

For tissue engineering purposes, scaffolds not only provide mechanical support to the cells, but actively influence cellular responses including cell attachment and proliferation. The scaffolds that can be used in the present invention can include natural or synthetic polymers, ceramics, and composites of ceramics and polymers. The DWJM can be used as a scaffold that attracts undifferentiated MSCs and murine osteoblasts and promotes their osteogenic and chondrogenic differentiation when the MSCs are exposed to the proper differentiation media. In addition, DWJM has favorable surgical characteristics including: porosity, poroelasticity, and compressibility, which makes it easily curved to irregular shapes.

DWJM can be used as a scaffold for growing cells in three dimensions. In this capacity, it can have applications related to tissue engineering, including bone and cartilage tissue regenerative applications, and including hair follicle generation when the mesenchymal cells are exposed to osteogenic differentiation medium. For example, engineering cartilage tissue can potentially help patients who suffer from osteoarthritis. On the other hand, engineering bone tissue can potentially treat bone defects that result from trauma, non-healing fractures, or pathological fractures. The DWJM can be used in supporting osteogenesis and chondrogenesis differentiation under certain conditions, and supporting osteogenesis and hair follicle genesis under certain conditions. These findings may have major applications in the future that span the fields of tissue engineering and 3D cell culture models, among others.

In one embodiment, a method of preparing a tissue scaffold having at least one cell type growing thereon to remodel the tissue scaffold can include: providing at least a portion of an umbilical cord; isolating the umbilical cord matrix of the umbilical cord; decellularizing the umbilical cord matrix; seeding at least one cell type on the decellularized umbilical matrix; expanding the cell population with growth medium; and immersing the seeded cell type in a differentiation medium to induce differentiation to a desired cell type. The umbilical cord matrix can be Wharton's Jelly Matrix, and when decellularized is DWJM. The seeded cell type is selected from the group consisting of mesenchymal stem cells, WJMSCs, MC3T3E1 cell line, smooth muscle cells, fibroblasts, chondrocytes, prechondrocytes, osteoblasts, endothelial cells, dendritic cells, keratinocytes, myogenic cells, stem cells, muscle cells, epithelial cells, and combinations thereof.

In one embodiment, the tissue scaffold can be induced to have osteogenic and/or chondrogenic differentiation. The differentiation medium is one or more of the following: osteogenic and/or chondrogenic differentiation media. The growth medium can be an expansion media, which can be a common cell culture expansion media. The osteogenic differentiation can produce bone, while the chondrogenic differentiation media can produce cartilage. The tissue scaffold having osteogenic and/or chondrogenic differentiation can be used for implantation into an bone and/or cartilage site in a subject. The scaffold portion having the osteogenic portion can be separated from the scaffold and used as a bone implant. The scaffold portion having the chondrogenic portion can be separated from the scaffold and used as a cartilage implant. The osteogenic portion and chondrogenic portion can be removed from the scaffold and used together in a bone implant and a cartilage implant. The osteogenic portion and chondrogenic portion can be used together for a bone-cartilage interface implant to be implanted at a location where bone and cartilage have an interface. While a portion of the scaffold can be used, the entire scaffold may be used in some instances. The osteogenic portion and chondrogenic portion can be used together or separately, in different locations, and in the same location so as to match the tissue receiving the implant. Accordingly, the osteogenic and/or chondrogenic scaffold can be used in methods of treating a disease, traumatic injury, bone or cartilage loss in a mammal by implanting the biological scaffold having an osteogenic portion and/or a chondrogenic portion. In one aspect, the scaffold to be implanted may only have an osteogenic portion. In one aspect, the scaffold to be implanted may only have a chondrogenic portion.

Experimental A—Hair Generation

Materials and Methods
Wharton's Jelly Mesenchymal Stromal Cell (WJMSC) Isolation IRB approval was obtained for human umbilical cord collection and mesenchymal stromal cell (MSC) isolation from the University of Kansas Medical Center (HSC #12129). The procedure described by Wang et al. was used for MSC isolation and expansion (Wang L, Singh M, Bonewald L F, Detamore M S. Signaling strategies for osteogenic differentiation of human umbilical cord mesenchymal stromal cells for 3D bone tissue engineering. J Tissue Eng Regen Med 2009; 3:398-404). Following these procedures, MSCs were plated in cell culture flasks and expanded to 80-90% confluence then passaged until fourth to seventh passage (P4-P7). Expansion media was composed of low glucose Dulbecco's Modified Eagle Medium (DMEM) with 10% fetal bovine serum (FBS) and 1% penicillin and streptomycin (Pen/strep) all purchased from Life Technologies (Grand Island, N.Y.).

WJMSC Culture and Osteogenic Differentiation to Generate Spheroids

Isolated WJMSCs were expanded in expansion medium and passaged until fourth to seventh passage (P4-P7) to prepare for osteogenic differentiation. $1 \times 10^6$ cells/mL in expansion media were added to each well of a 24 well non-tissue culture treated plate and incubated at 37° C. and 5% $CO_2$. After two days, the medium was changed to osteogenic medium, consisting of culture medium (e.g., low-glucose DMEM) supplemented by 100 nM dexamethasone (DEX; Sigma, St. Louis, Mo., USA), 5 mM B-glycerophosphate (β-GP; Sigma), 10 nM 1α,25-hydroxyvitamin D3 (VD3; Biomol International, Plymouth Meeting, Pa., USA) and 50 μg/mL ascorbic acid 2-phosphate (AA2P; Sigma). Exposure to osteogenic differentiation media continued up to 4 or 5 weeks. Longer exposure to the osteogenic differentiation media may also be employed.

DWJM Scaffold Preparation

Umbilical cords were immediately collected after normal vaginal delivery and placed in a premade transfer solution made of physiologic saline containing Amphotericin B, penicillin and streptomycin at 4° C. Within 72 hours, the decellularization process was started. In the decellularization process and under aseptic conditions in a biohood cabinet, pieces of fresh Wharton's jelly matrix were aseptically dissected from the cord, separated from the blood vessels in pieces (approximately 5×30 mm) and decellularized in a custom apparatus. The decellularization process (patent pending, see Hopkins U.S. 2011/0165676, which is incorporated herein by specific reference in its entirety) included multiple osmotic shock cycles using hypertonic and hypotonic solutions, a non-ionic detergent (Triton-x) and an anionic detergent (sodium lauroyl succinate) as well as an enzyme digestion with recombinant endonuclease (Benzonase™). All process residuals were removed with 36 hours of iterative solvent washouts (double deionized water and 40% ethyl alcohol) dialyzed against hydrophobic and ion exchange resin beads (IWT® TMD-8, Amberlite™ XAD16, Powex™ 550A Biobeads, all Sigma Aldrich). Prior to seeding, under a laminar flow hood, DWJM fragments were transferred to a large Petri dish and covered with phosphate buffered saline (PBS). Using a sterile 5 mm or 7 mm skin punch biopsy kit, 5 mm or 7 mm in diameter pieces were obtained and then washed with PBS twice. The height of the DWJM pieces ranged from 2-3 mm when cut with scissors. When the WJMSCs were ready to be seeded, the DWJM pieces were moved to a non-tissue culture treated plates.

DWJM Cell Seeding and Osteogenic Differentiation

Prior to seeding, the DWJM scaffolds were immersed in the expansion medium in a 24 well non-tissue culture treated plate and incubated for 1 day at 37° C. with 5% $CO_2$. The expansion medium was subsequently removed from the scaffolds prior to seeding. P4-P7 WJMSCs were then resuspended in expansion medium and seeded by repeated pipetting into the DWJM scaffold at a $20 \times 10^6$/mL DWJM scaffold seeding density or $2 \times 10^4$/mm$^3$ DWJM. This was followed by incubation on an orbital shaker at 50 rpm. After 4 hours, expansion medium was added to completely immerse the scaffold in a total of 1 mL. After two days, the expansion medium was changed to osteogenic medium, with the osteogenic medium being a culture medium (e.g., low-glucose DMEM) supplemented by 100 nM dexamethasone (DEX; Sigma, St. Louis, Mo., USA), 5 mM B-glycerophosphate (β-GP; Sigma), 10 mM 1α,25-hydroxyvitamin D3 (VD3; Biomol International, Plymouth Meeting, Pa., USA) and 50 μg/mL ascorbic acid 2-phosphate (AA2P; Sigma). Exposure to osteogenic differentiation continued for up to 4 or 5 weeks.

Histology

Spheroids:

The spheroids generated from these experiments were scraped from the bottom of the culture well and transferred to PreservCyt Solution® (Cytyc Corporation (Hologic), Marlborough, Mass.) and processed using Cellient Automated Cell Block System®. Eosin was applied and vacuum-drawn through the sample to visualize the cells. After isopropyl alcohol dehydration and xylene clearing, the samples were embedded in paraffin.

DWJM:

The DWJM material was fixed in either formalin or 4% paraformaldehyde, embedded in paraffin, sectioned, and stained as described.

Alizarin Red Stain:

Alizarin Red Stain was performed using the American Mastertech (Lodi, Calif.) Alizarin Red Stain kit per manufacturer instructions. Slides were reviewed using Olympus BX40 microscope and pictures were taken using DP72 digital camera.

Immunohistochemistry

Cytokeratin 19 (CK19) monoclonal mouse anti-human antibody (Dako, DK-2600 Glostrup, Denmark) was used for immunohistochemical staining. Also, Goat polyclonal antibody BMP-4 (Santa Cruz Biotechnology, Santa Cruz, Calif.), Versican rabbit polyclonal antibody, and shh antibody (Santa Cruz Biotechnology) were used for immunohistochemical staining of micron deparaffinized paraffin sections. Epitope retrieval was performed in Biocare Decloaking Chamber (pressure cooker), under pressure for 5 min, using Dako EnVision Flex high pH buffer or using pH 6.0 citrate buffer followed by a 10 minute cool down period. Endogenous peroxidases were blocked with 3% $H_2O_2$. In one procedure, cytokerain 19 (clone RCK108) was used as the primary antibody for 20 minutes, followed by FLEX enVision HRP detection for 30 minutes and FLEX DAB for 5 minutes. As an enhancing reagent, 2% $CoCl_2$ was added for 5 minutes. A hematoxylin counterstain was used.

In another set, primary antibody incubation with BMP-4 (1:50, 60"), Versican (1:1000, 30") or SHH (1:100, 60"), was followed by Vector ImPRESS anti-goat (Vector Laboratories, Burlingame, Calif.) or MACH2 Rabbit HRP Polymer detection (Biocare Medical, Concord, Calif.) for 30 minutes and DAB+ (Dako, Carpinteria, Calif.) for 5 minutes. Immunohistochemical staining was performed using the IntelliPATH FLX Automated Stainer at room temperature. A light hematoxylin counterstain was performed, following which the slides were dehydrated, cleared, and mounted using permanent mounting media. Slides were reviewed using Olympus BX40 microscope and pictures were obtained using DP72 digital camera.

FACS

For MSC phenotype, the following primary and secondary antibodies were used: anti-CD 34-phycoerythroin (PE), anti-CD 45-PE, anti-CD 105-PE, anti-CD 73-PE, anti-CD 90-PE, and mouse IgG1-κ-PE isotype control (BD Biosciences). Flow cytometry was performed using FACScan (BD, San Jose, Calif.) and the data was analyzed using CELLQuest Version 3.2.1 (BD).

ELISA

Culture supernatant was collected weekly prior to media change. Bone morphogenetic protein-4 human-ELIS kit (BioVendor LLC. Cat#BBT0314R) was used and samples (n=3 for each time point) were processed according to manufacturer's recommendations.

Western Blot

Seeded scaffolds (n=3 for each time point) were collected at 0, 2 and 4 weeks of osteogenic differentiation. Sterile scissor was used to cut each scaffold into small pieces and a pestle was used to homogenize the sample. Samples were lysed in 30 µl of Radio Immuno Precipitation Assay (RIPA) buffer (Sigma-Aldrich), separated by SDS-PAGE gel electrophoresis, transferred to an Immobilon Polyvinylidene difluoride membrane (Milipore), and immunoblotted with primary antibodies against versican (#: 1677.00.02, 1:10000; Sdix) and BMP4 (#: MAB1049, 1:10000, Milipore) and secondary anti-mouse IgG-HRP (#7076, 1:40000, Cell Signaling).

Statistics

All data were expressed as means±one standard deviation. Pearson's r coefficient was used to study the relationship between average BMP-4 concentration and culture time. Two-tailed p value was calculated and statistical significance was determined by a statistical threshold of $p<0.05$. The statistical analysis was performed utilizing Graphpad Prism software version 6 (GraphPad Software, Inc.)

Results

Characteristics of DWJM

Figure 1B:
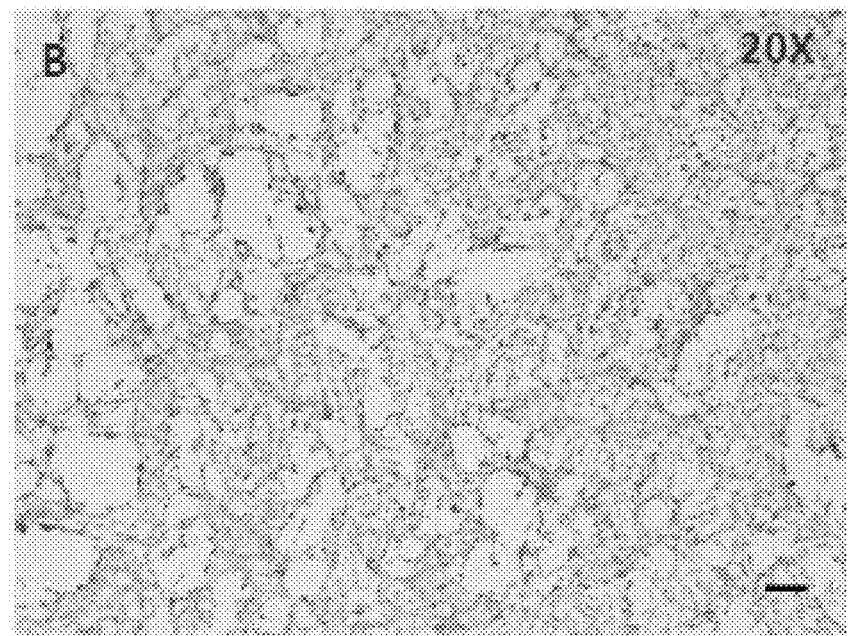
FIG. 1B includes an image of DWJM without CK19 cells.

To evaluate DWJM for any remaining cells or any CK19-positive cells in specific, we stained DWJM samples for CK19. H&E stained sections revealed no intact cells and no CK19-positive cells were detected in DWJM (see FIGS. 1A and 1B). Decellularized Wharton's jelly matrix was prepared before seeding. This H&E stained section of DWJM (see FIG. 1A) shows no cellular elements. No CK19-positive cells/structures were recognized in CK19 stained sections of DWJM before seeding (see FIG. 1B). Scale bars represent 50 mm in FIGS. 1A and 1B.

WJMSCs Expressed Mesenchymal Stromal Cell Phenotype

Flow cytometry tests confirmed that the expanded population was negative for CD34 and 45 and positive for CD73, CD90 and CD105 (data not shown). This is consistent with an MSC profile. In addition, the isolated WJMSCs were selected based on their adherence to plastic surfaces in culture flasks. Finally, the isolated WJMCs demonstrated evidence of osteogenic differentiation based on positive alizarin red staining (described later) following their exposure to the osteogenic differentiation medium. Together, these findings support the conclusion that the isolated and expanded WJMSCs represent true MSCs.

Spheroid Structures Express CK19-Positive Cells in a Diffuse Pattern

In spheroids, CK19-positive cells were expressed abundantly, however, in a diffuse fashion. Their expression seems to correspond to the cellular areas of the spheroids. In addition, areas of possibly nascent hair structures were seen in close proximity to areas of alizarin red stain and areas of CK19 cell expression. These CK19-expressing cells appeared to coalesce and produced a centrally located clear area on cross sections (see FIG. 4C).

DWJM Expresses CK19-Positive Cells in a More Discrete Fashion

Figures 5A, 5B:
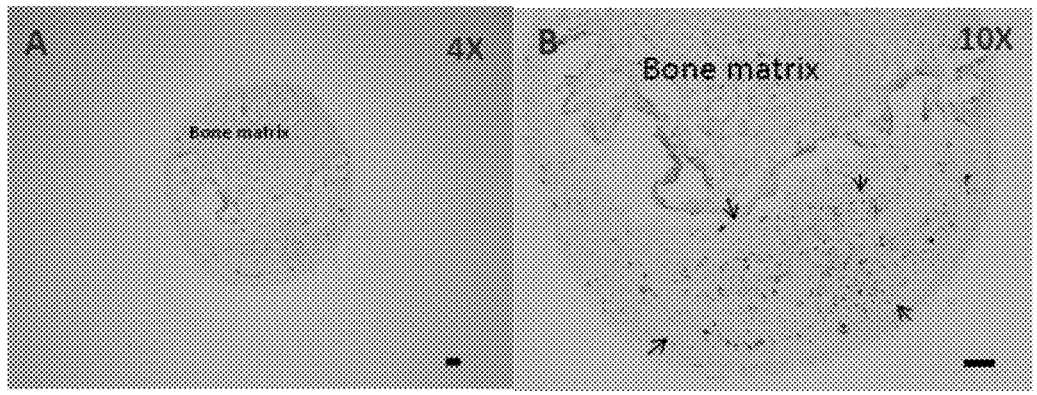
FIGS. 5A-5F include images showing a DWJM having CK19-positive cells and bone matrix.
Figures 5C, 5D:
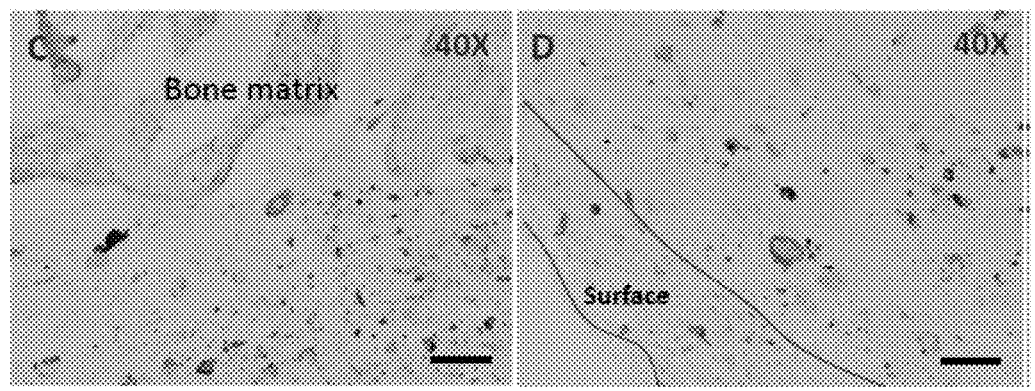

In 5 week DWJM, CK19 expression seemed to be more discrete, predominantly on the outer surface of the DWJM and in a discrete area between the surface and what appears as a matrix material (see FIG. 5B and FIG. 5D). In this 5 week matrix material, there were no indications of hair structures, although the CK19-expressing cells that appeared coalesced and produced a centrally located clear central area resembling the structures seen in spheroids.

Figures 2A, 2B:
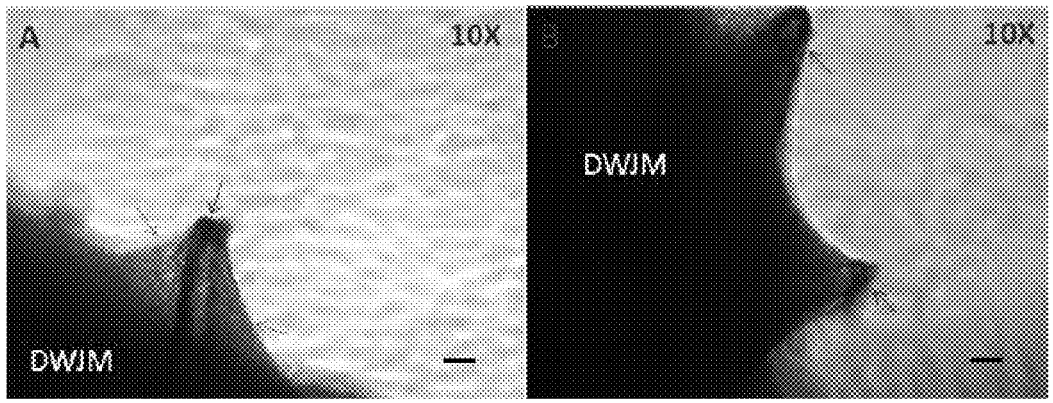
FIGS. 2A-2F include images that show hair-like structures protruding from DWJM.

We repeated the experiments using DWJM for seeding, followed by osteogenic differentiation. At two weeks after starting osteogenic differentiation, we noticed hair-like structures either protruding to or through the outer layer of the matrix material (see FIG. 2). In some areas the hair appeared thicker and straight and able to protrude through the outer layer of cells and the hair structures having a width of about 100 µm (see FIG. 2A), while in other areas, hair structures appeared thinner and coiled under the outer layer of cells with these hairs structures having a width of about 30 µm (see FIG. 2B). Under dissecting microscope the hair structures were either protruding through the outer layer of the matrix or causing outside protrusions. They were either protruding through the outer layer of the matrix in the case of the thicker and the more straight structures (see FIGS. 2C-2E), or simply caused an outside protrusion (see FIG. 2F). These structures were ≤100 micrometer in diameter, which is consistent with the diameter of hair as reported in the literature (Saint Olive Baque C, Zhou J, Gu W, et al. Relationships between hair growth rate and morphological parameters of human straight hair: a same law above ethnical origins? International journal of cosmetic science 2011). Bulbous structures communicated with the outside of the DWJM structure. These areas were closely associated with CK19-expressing cells. Hair-like structures were occasionally straight or coiled but strongly positive for CK19.

Figures 2C, 2D:
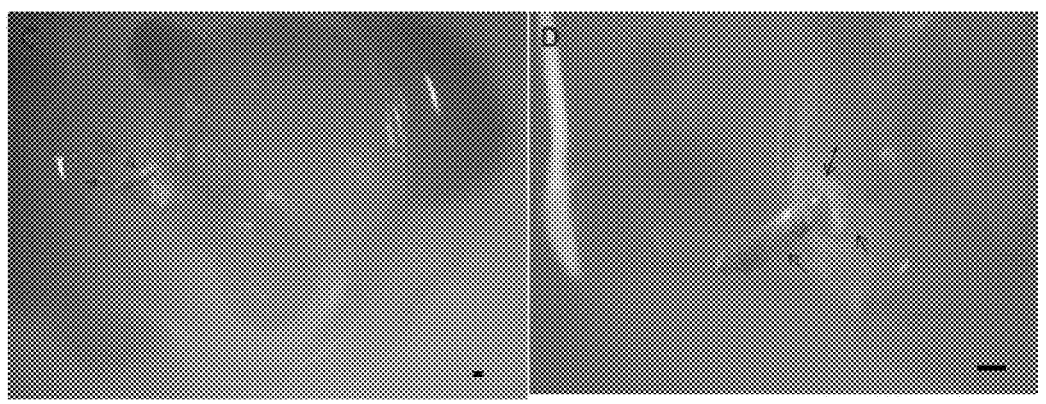
Figures 2E, 2F:
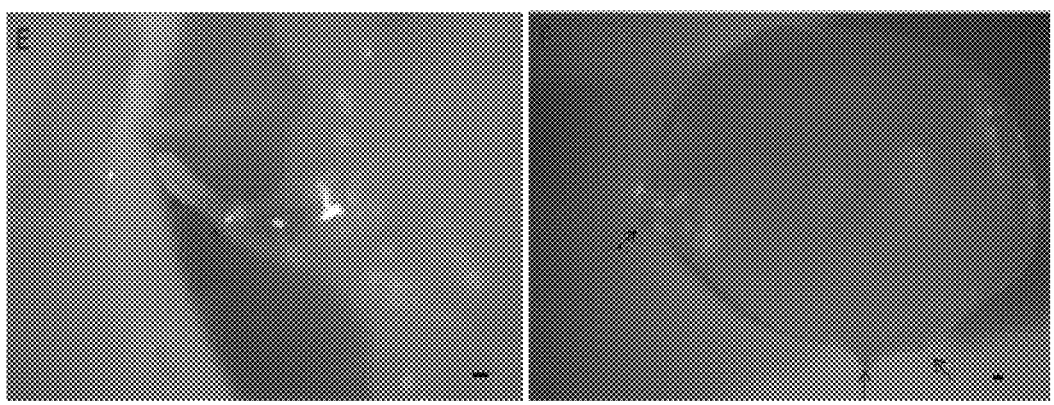

FIGS. 2A-2E cooperatively show patterns of hair-like structures in DWJM. Hair-like structures were observed growing out of DWJM 2 weeks following WJMSC seeding and osteogenic induction. In phase-contrast microscopy pictures (see FIG. 2A-2B) taken during culture, hair-like structures were observed to grow under the outer layer of the DWJM and in some cases either successfully protruded through the outer layer (see FIG. 2A) or just caused a protrusion of the outer layer of DWJM (see FIG. 2B). Also, the hair-like structures were either straight (see FIGS. 2A and 2C-2E) or coiled (see FIG. 2B). The arrows in FIG. 2A pointing to the sides of the protrusion point to the outer layer covering DWJM. The hair-like structure caused the outer layer covering DWJM to appear lifted up as shown. In this DWJM, 2 hair-like structures protruded through DWJM (arrows pointing to protrusion that appears to have hair in it) seen in (FIGS. 1A and 2C-2E). A second hair-like structure (arrows) protruded through the outer layer of DWJM; however, this hair-like structure was surrounded by tissue material (see FIG. 2E). In FIG. 2F, multiple areas of protrusions noted (arrows). In FIGS. 2C-2E pictures, material was visualized using Nikon SMX1500 dissecting microscope and pictures were taken using Optem DC50NN camera. Scale bars in FIGS. 2A-2F represent 100 mm.

Hair-like structures in WJMSC spheroids underwent osteogenic differentiation. To rule out an effect of the DWJM, the cells were cultured without the DWJM. WJMSCs were cultured in nontissue culture plates; similar to earlier experiments, we induced osteogenic differentiation using the same osteogenic medium components. In the WJMSC spheroids a similar phenomenon occurred, where hair-like structures were found on histologic sections of these spheroids (see FIG. 3). The hair structures were never found in the core of the spheroid, but rather were always located close to the surface. Within the same peripheral region of the spheroid and adjacent to the hair-like structures were large regions of calcification (lower arrows in 40× panels). Staining with alizarin red clearly highlighted the areas of calcification, also found along the periphery of the spheroid.

Figure 3:
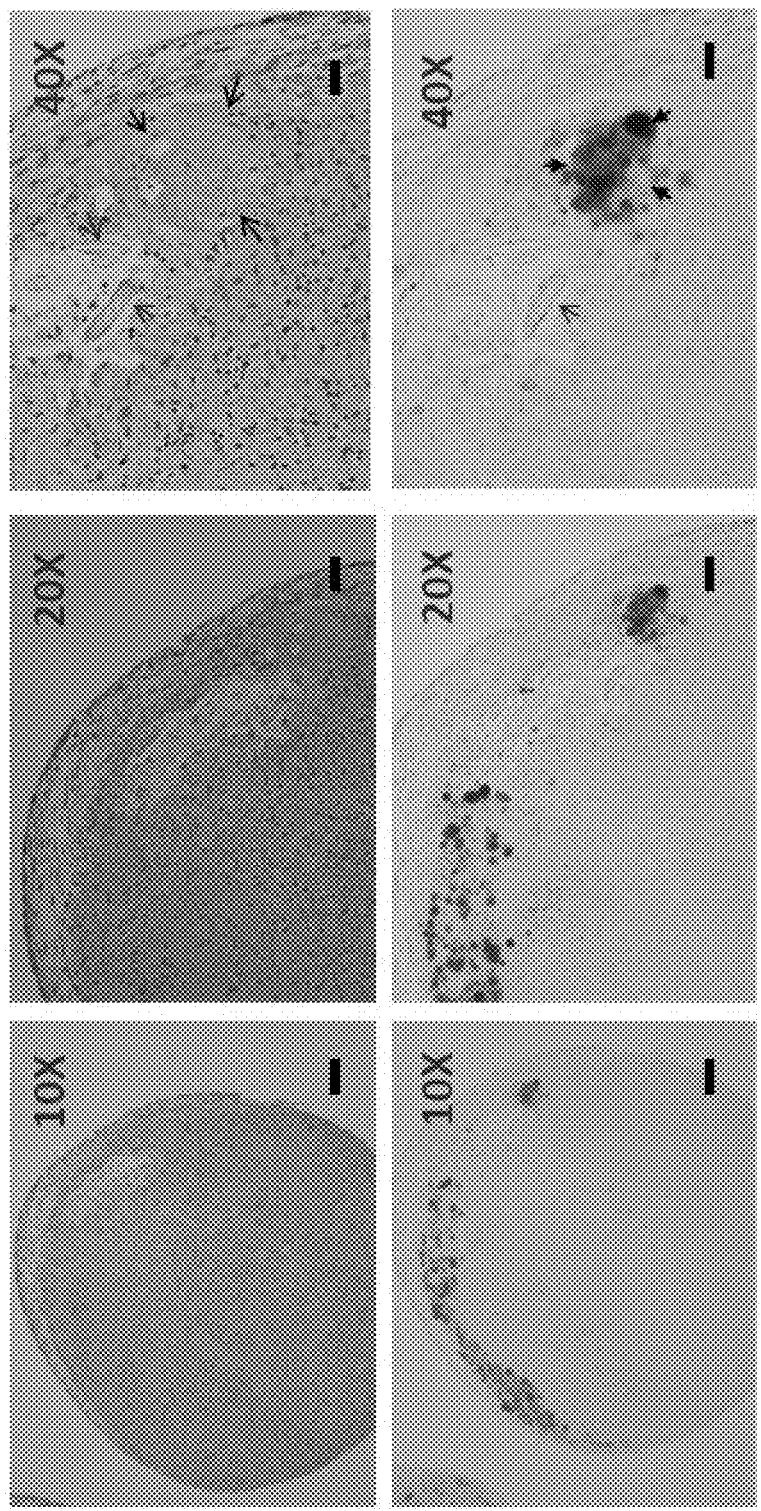
FIG. 3 includes images that show hair structures and CK19-positive cells in osteogenic differentiated WJMSC spheroids.

FIG. 3 shows hair structures and CK19-positive cells in osteogenic differentiated WJMSC spheroids. In the upper panel, H&E stained slides demonstrated areas of calcification (lower arrows in 40× panels) in close proximity to hair-like structures (upper arrows in 40× panels) within the osteogenic differentiated spheroids. In the lower panel, alizarin red stained slides demonstrated areas of mineralization (black arrows) within the calcified areas. The areas of mineralization appeared to be in close proximity to the hair structures (upper arrows). Scale bars in FIG. 3 represents 100, 50, and 25 mm in 10×, 20×, and 40×, respectively.

Expression of CKs in cells associated with hair-like structures. Since hair is an ectodermal structure made of keratins by hair follicles, expression of CK15 and CK19 can be used as biomarkers of hair follicles. CK19 is considered a marker of hair follicle stem cells. Likewise, CK15 is considered one of the markers of the bulge cells in human hair follicle. These bulge cells have properties of stem cells as they have high proliferative capacity and are multipotent capable of regenerating ectodermal structures, such as hair follicles, sebaceous glands, and epidermis. Spheroid structures were expressed CK19-positive cells in a diffuse pattern. In WJMSC spheroids, CK19-positive cells were expressed in an abundant although diffuse fashion (see FIG. 4B). These CK19-expressing cells appeared to coalesce producing a centrally located clear area on cross sections (see FIGS. 4A and 4C). In the case of WJMSC spheroids, we confirmed CK19 expression by western blot analysis (see FIG. 4B). Interestingly, the expression of CK19 clearly increased over time following exposure to osteogenic media (see FIG. 4B). These findings suggest that exposure of WJMSCs in their spheroids to osteogenic differentiation media led to further differentiation of WJMSCs to CK19-positively expressing cells.

Figure 4A:
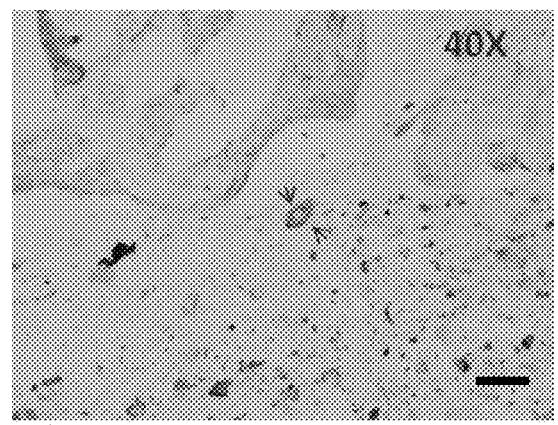
FIG. 4A includes an image that shows DWJM having CK19-positive cells.
Figure 4B:
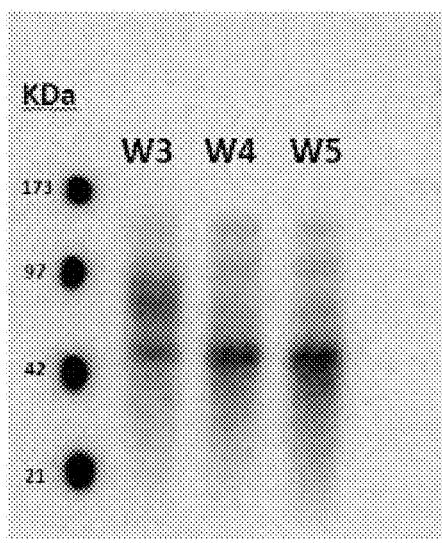
FIG. 4B includes an image of a Western blot that shows expression of CK19.
Figure 4C:
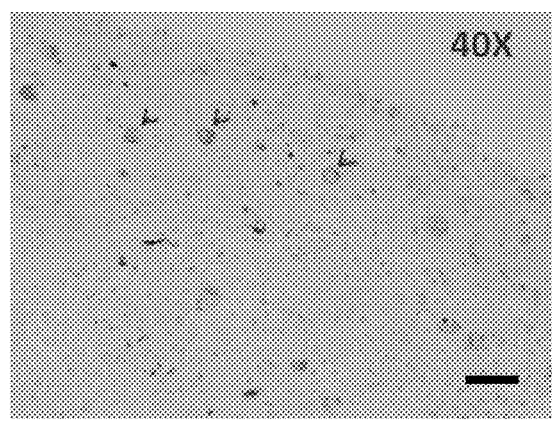
FIG. 4C includes an image that shows spheroids having CK19-positive cells.

FIGS. 4A-4C cooperatively illustrate that CK19-positive cells in DWJM and spheroids resemble hair follicle structures. CK19-positive cells coalesced and formed round structures with central clearings, resembling hair follicle structure in both DWJM (see FIG. 4A) and spheroids (see FIG. 4C with arrows point to these structures). Scale bars in FIGS. 4A and 4C represent 50 mm. CK19 expression was confirmed by western blot at 3, 4, and 5 weeks of osteogenic differentiation time points (see FIG. 4B). A band with approximate molecular weight of 40 KDa was detected. The calculated western blot's band density for weeks 3, 4, and 5 of osteogenic differentiation using ImageJ is shown. Band density for CK19 expression clearly increased over time.

Figures 5E, 5F:
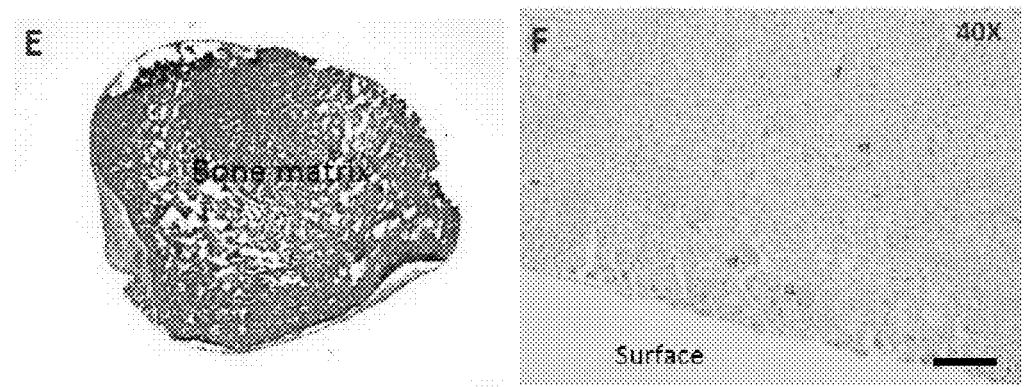

DWJM expressed CK19-positive cells in a more discrete fashion. FIGS. 5A-5F cooperatively show a pattern of CK19 expression in DWJM following osteogenic differentiation media. In these pictures, CK19-positive cells appeared to concentrate predominantly in 2 areas: around the DWJM structure as seen in FIG. 5A and FIG. 5D, which shows the outer surface of DWJM; and in a very discrete area adjacent to the more central bone matrix area as seen in (see FIGS. 5B, 5C, and 5D). Artificial lines are used to distinguish the surface area from the area of CK19 cell condensation (marked by black arrows) in FIG. 5D. The bone matrix area stained positive (dark brown) for collagen I (see FIG. 5E) and negative for alizarin red (see FIG. 5F). However, alizarin red stain brought out the large structures of CK19 positivity with central clearing (see arrows in FIG. 5F). Scale bars in FIGS. 5A, 5B, and 5E represent 100 mm and in FIGS. 5C, 5D, and 5F represent 50 mm.

In DWJM, CK19 expression was predominantly closer to the surface of the DWJM and in discrete areas between the surface and what appears to be a bone matrix material evident by collagen I staining (see FIG. 5E). We stained for collagen I as it is considered the most abundant bone matrix protein. Alizarin red staining, on the other hand, was negative in DWJM. However, the Alizarin red stained sections brought out the large structures of CK-positivity with central clearing. In some sections, there were no indications of hair structures, although the CK19-expressing cells were seen. These CK19-positive cells appeared coalesced and produced a centrally located clear central area resembling the structures seen in spheroids. In DWJM tissue sections, bulbous structures were noted. These structures that resemble the hair follicle communicated with the outside of the DWJM structure (see FIG. 6), which were closely associated with CK19-expressing cells.

Figure 6:
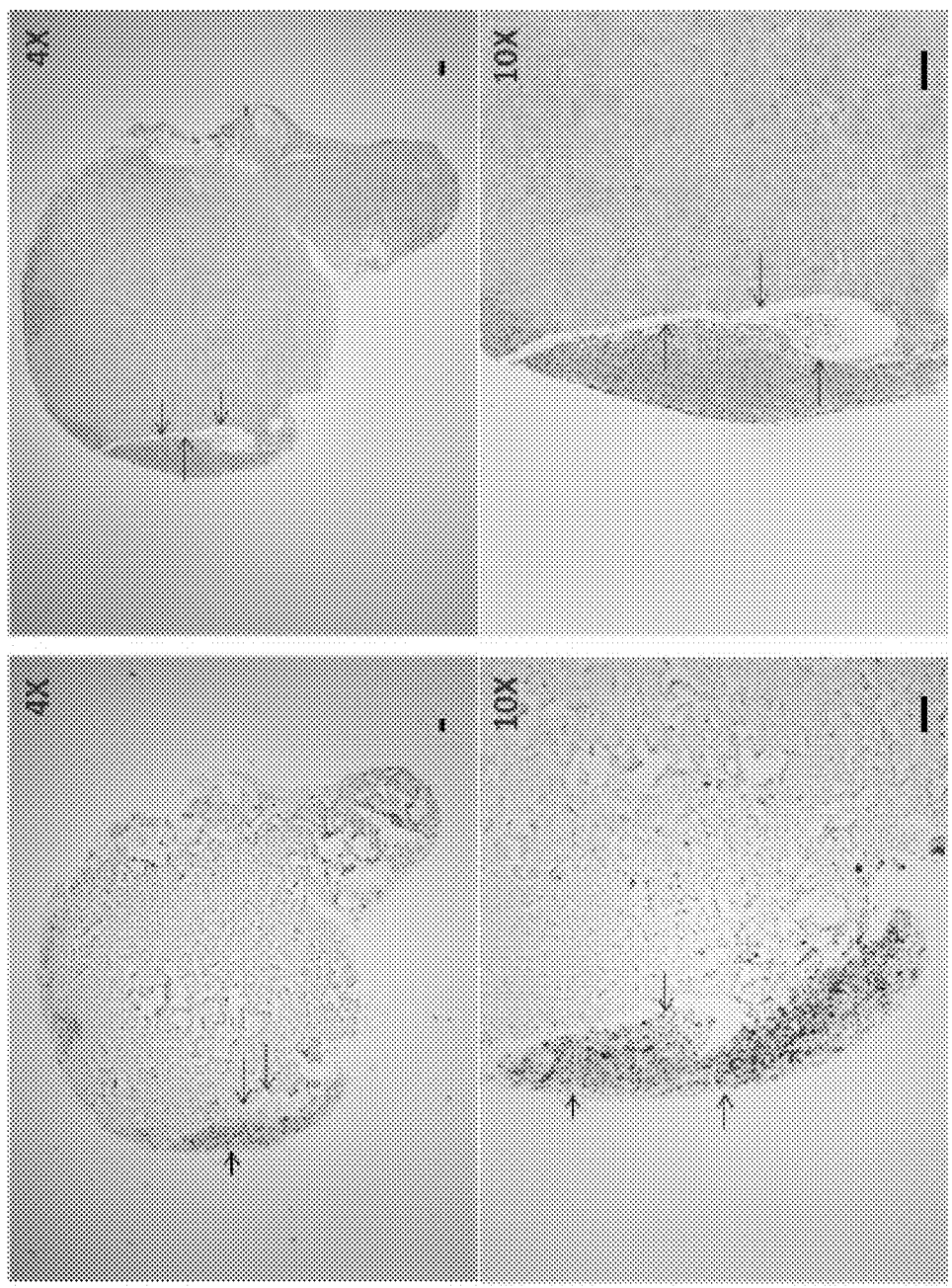
FIG. 6 includes an image that shows areas of defects in DWJM resembling hair follicle structure associated with CK19 expression.

FIG. 6 shows areas of defects in DWJM resembling hair follicle structure associated with CK19 expression. Defect areas (outlined by internal arrows) within the DWJM were seen in H&E-stained and CK-stained sections. These areas resembled hair follicle structure. The hair structures were not identified in these sections. It is thought that specimen processing lead to their expulsion from DWJM. The CK19-expressing cells were associated with these defects (outside black arrows point to defects). Objective lens magnifications are included in the graphs. Scale bars represent 100 mm.

Figure 7A:
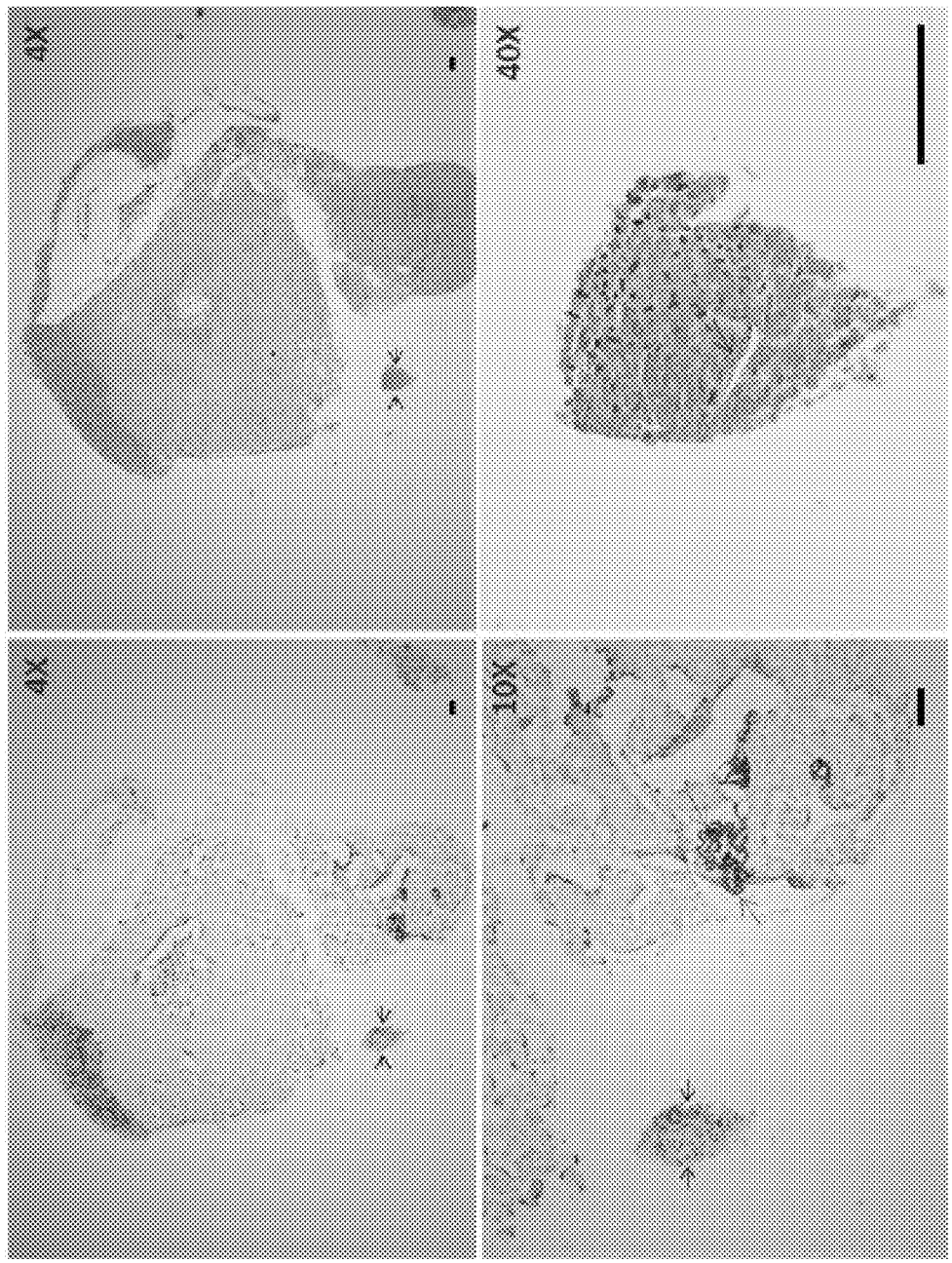
FIG. 7A includes images that show hair-like structures identified in DWJM associated with CK19 expression.

Hair-like structures were associated with CK19-positive cells. These hair-like structures were either straight or coiled (see FIG. 7A), but strongly positive for CK19 in the case of the latter. Positive staining for CK19 confirms that the structures represent keratinized material. FIG. 7A shows hair-like structures identified in DWJM associated with CK19 expression. A CK19 strongly expressing collection of cells (see arrows point at "floating" portion) was found to include a straight hair-like structure (arrow of 40× panel). On the other hand, a coiled CK19-positive hair-like structure was observed in another section (see arrows in 10× panel). Scale bars in FIG. 7A represent 100 mm. On histologic sections, the straight hair ranged from 4 to 53 mm in width and the coiled hair ranged from 12 to 24 mm in width.

Figure 7B:
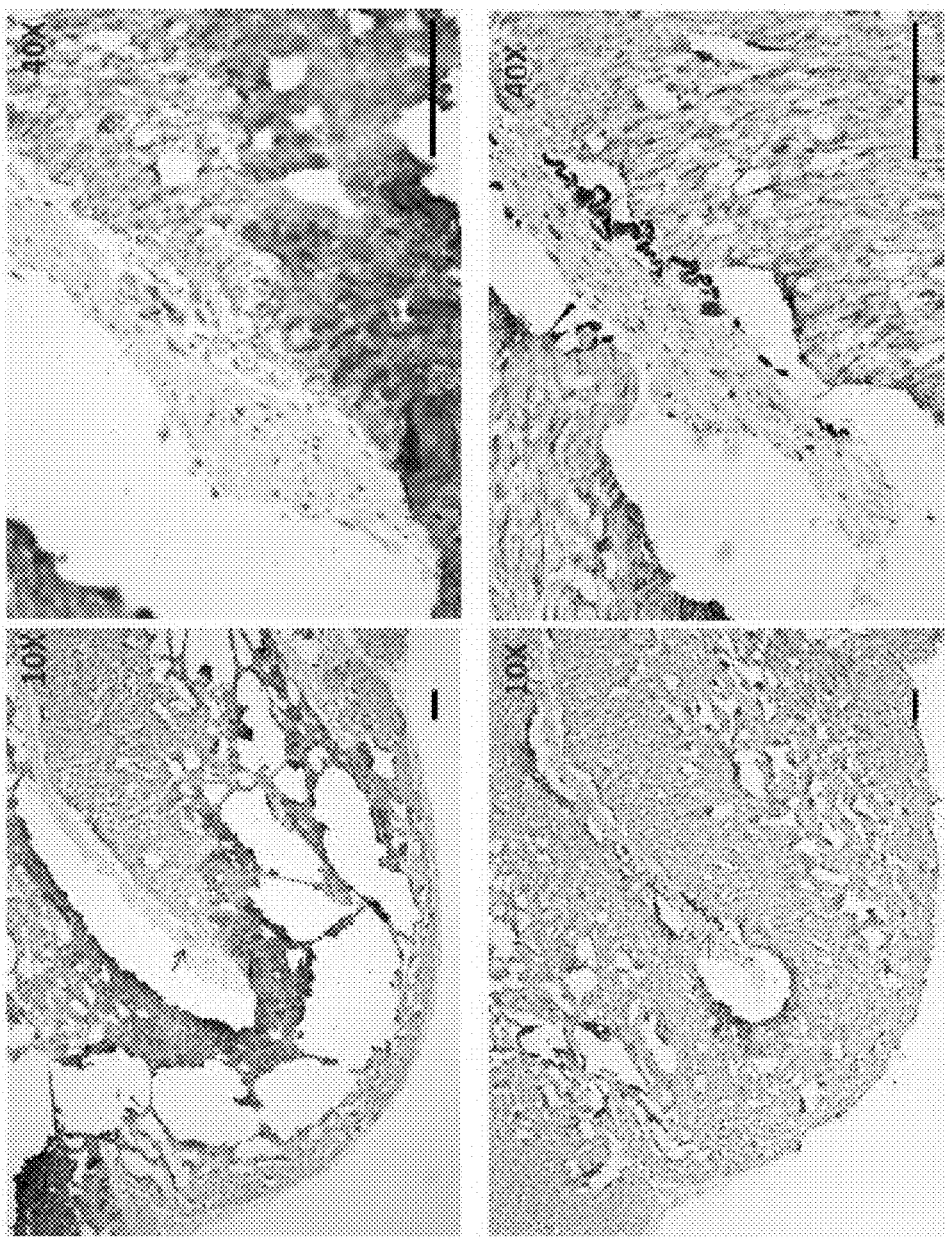
FIG. 7B includes images that show the CK15 and CK19 staining of DWJM sections.

Additionally, it was determined that cells expressing CK15 and CK19 were present in the DWJM. Interestingly, very few cells/structures stained positive for CK15. These CK15-positive cells/structures were located in sections, where the more abundant CK19-positive cells were observed (see FIG. 7B). This spatial closeness is a clue that these cells might truly reflect hair follicle cells. In addition, coiled hair-like structures were seen in close proximity to CK19-positive cells, which provides another clue that these were hair follicles capable of producing keratinized material. FIG. 7B shows the CK15 and CK19 staining of DWJM sections. The upper panels represent CK15-stained sections and the lower panels represent CK19-stained sections of DWJM. In these images, CK15-positive cells/structures (arrows in top 10× panel) appear to be seen in the same sections, where CK19-positive cells/structures (arrows in bottom 10× panel) were identified. However, the frequency of CK15-positive cells appears to be less than CK19-positive cells in these sections. Scale bars represent 100 mm.

Versican Expression

Figure 8A:
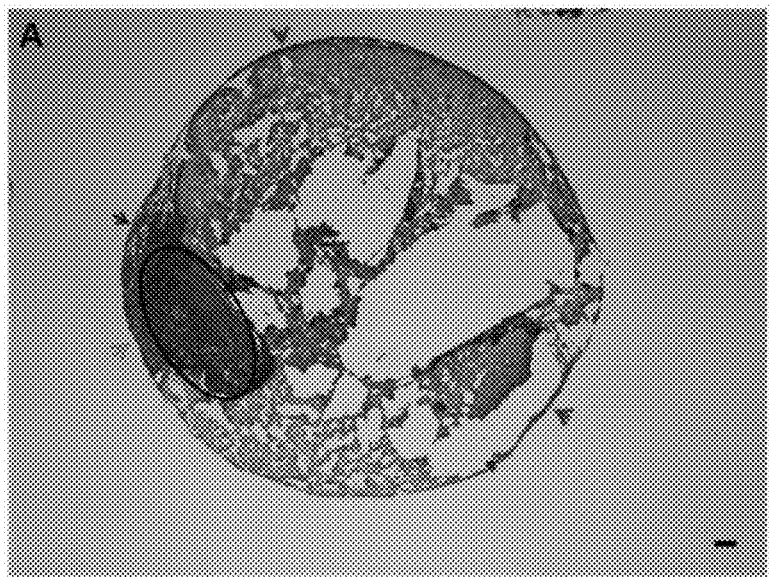
FIG. 8A includes an image that shows versican expression areas.
Figure 8B:
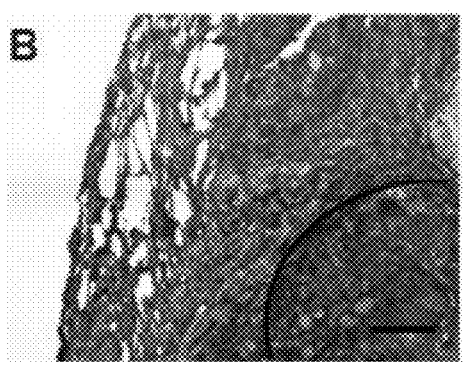
FIG. 8B includes an image that shows versican expression in a matrix rich cell condensation area.
Figure 8C:
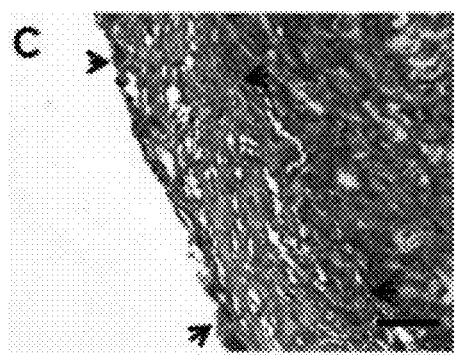
FIG. 8C includes an image that shows versican expression by multi-layered cells overlying an area of cell condensation.
Figure 8D:
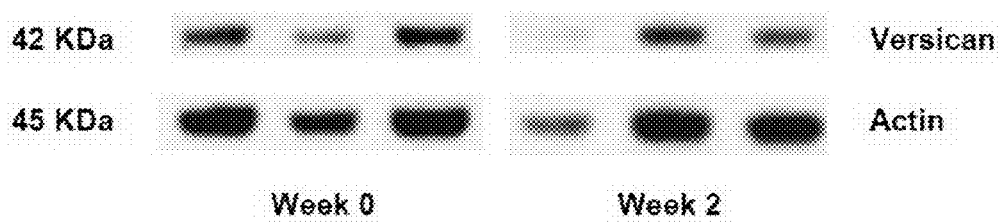
FIG. 8D includes an image of a Western blot showing versican and actin expression at week 0 and week 2.

It was found that abundant versican expression occurred in areas of cellular condensation with overlying multilayered spindle-like cells which are equivalent to dermal papilla and overlying layer of hair placode. Versican expression was very distinctively expressed by cells and intracellular matrix in the area of cell condensation and the overlying multi-cell layers (see FIG. 8A). In FIG. 8A, versican is strongly expressed in an area (marked with circular black line), resembling cell condensation. Versican expression is also noted in the multi-layered cells (bottom left arrow pointed to circled region) overlying the cell condensation area and to lesser extent the single layered surface layer of cells (outer arrows) that cover the rest of the DWJM. Versican positive cells overlying the cell condensation area exhibited different morphology according to their distribution (see FIG. 8B). In FIG. 8B, there is strong versican expression in the matrix rich cell condensation area (marked with curved black line), the adjacent cuboidal cells, and the spindle-like surface cells. There were cuboidal cells on both sides of the cell condensation area while spindle-like surface cells covered the cell condensation area. In addition, versican expression was noted by mono-layered cells surface covering DWJM outside the area of cell condensation. In FIG. 8C, versican expression by the multi-layered cells (black arrows) overlying the cell condensation area. In FIG. 8D, Western blot demonstrated several bands of osteogenic differentiation, where a dominant approximately 55 KDa band was demonstrated in control (week 0) and after 2 and 4 weeks (not shown) of osteogenic differentiation. Additional bands approximately 135, 85, and 39 KDa were mostly observed week 4 of osteogenic differentiation. Versican is known to present in various splicing variants in different tissues, accordingly, it is conceivable that the different bands we have demonstrated reflect splicing variants of this specific structure/tissue. Scale bar represent 100 microns in FIG. 8A, and 50 micron in FIG. 8B and FIG. 8C.

Sonic Hedgehog Expressed by Cell Condensation and Overlying Layer

Figure 9A:
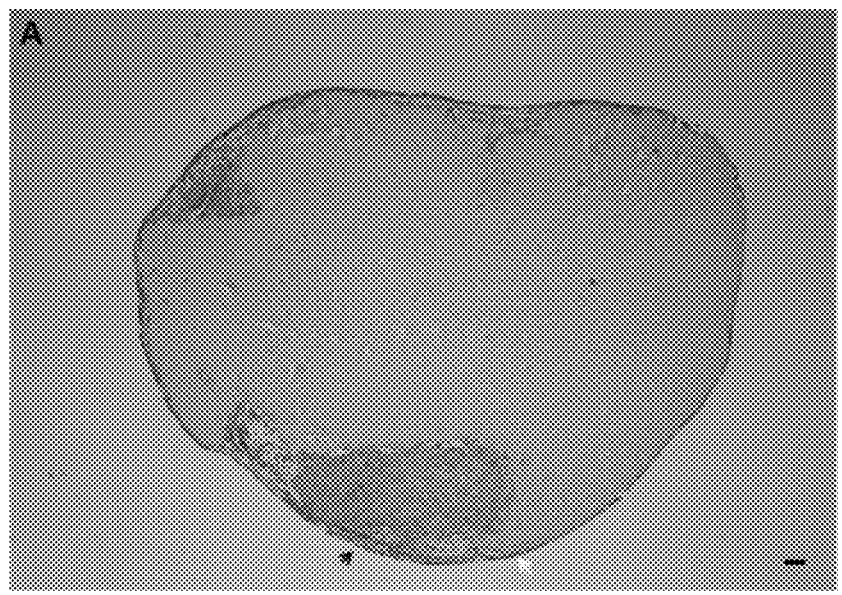
FIGS. 9A-9C include images of areas of shh expression.
Figure 9B:
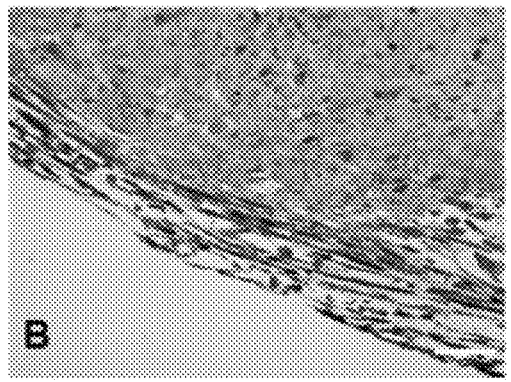
Figure 9C:
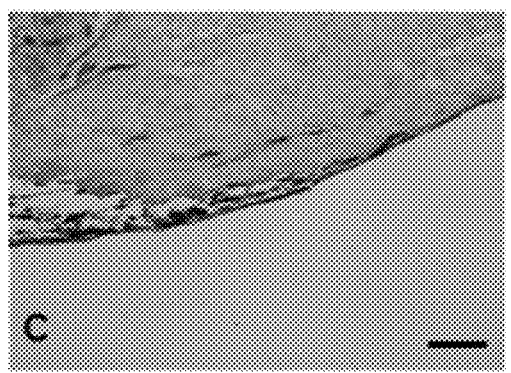

By examining histologic sections of our model, shh expression was noted in: the area of cell condensation, in the multi-layered cells overlying the cell condensation area, and in the monolayer of cells covering the rest of DWJM (see FIGS. 9A-9C). In FIG. 9A, hedgehog staining was identified in cell condensation area, in the multi-layered cells overlying the cell condensation area and to lesser extent in the single layered surface layer of cells that covers the rest of the DWJM. In FIG. 9B, there is strong shh expression in the matrix rich cell condensation area and the spindle-like surface cells. In FIG. 9C, shh expression was noted in the single cell layer surrounding DWJM outside the cell condensation area. Scale bar 100 microns for FIG. 9A and 50 microns for FIG. 9B and FIG. 9C.

Figure 10A:
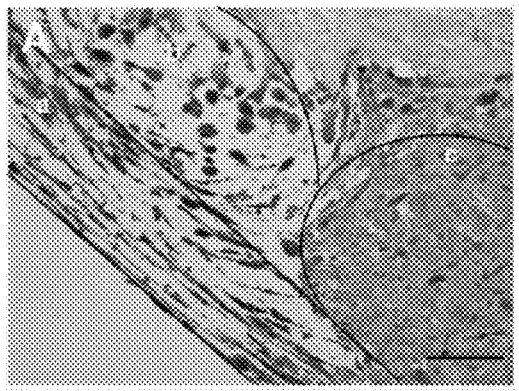
FIGS. 10A-10E include images of cellular patterns in the DWJM with areas of shh expression.
Figure 10C:
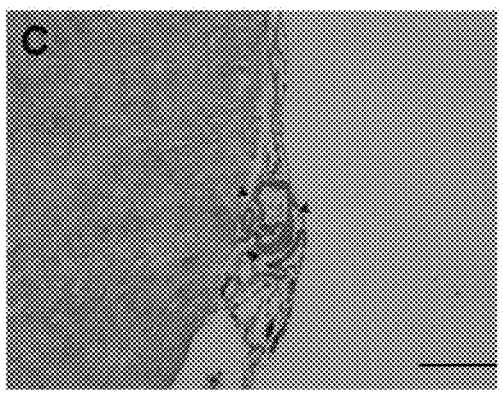
Figure 10B:
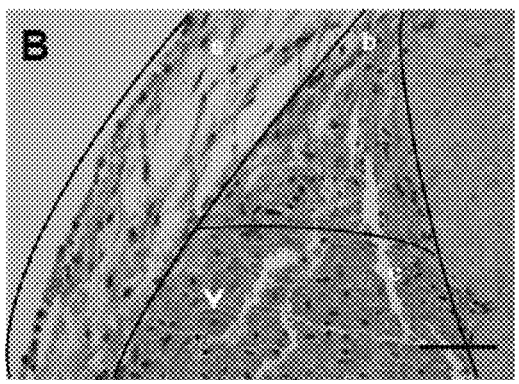
Figure 10D:
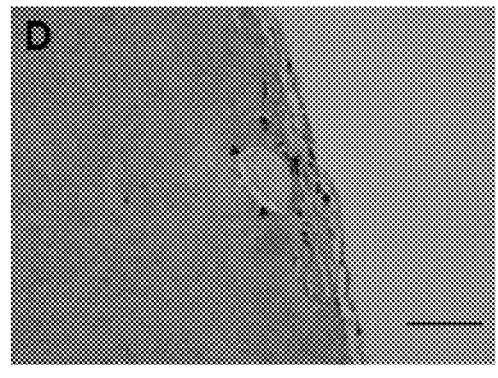
Figure 10E:
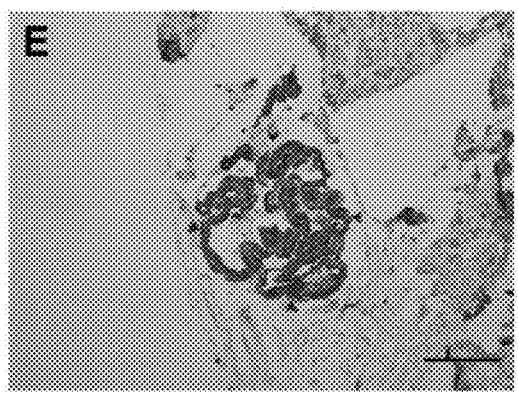
Figures 11A, 11B:
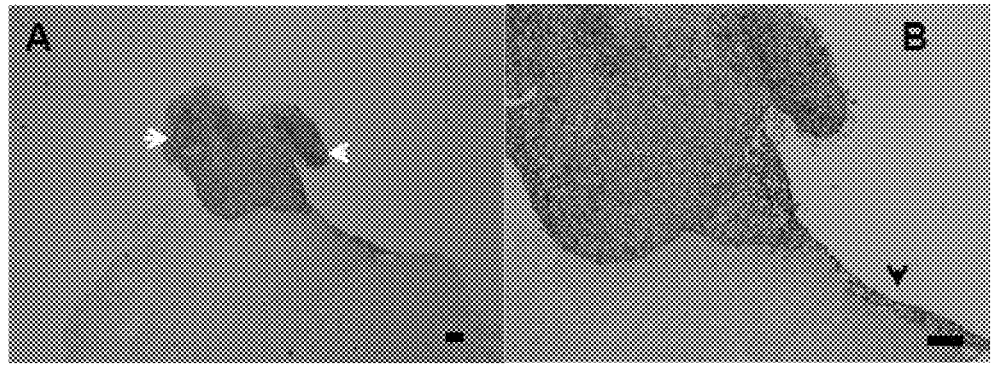
FIGS. 11A-11F include images of WJMSCs forming cellular clumps in DWJM.
Figures 11C, 11D:
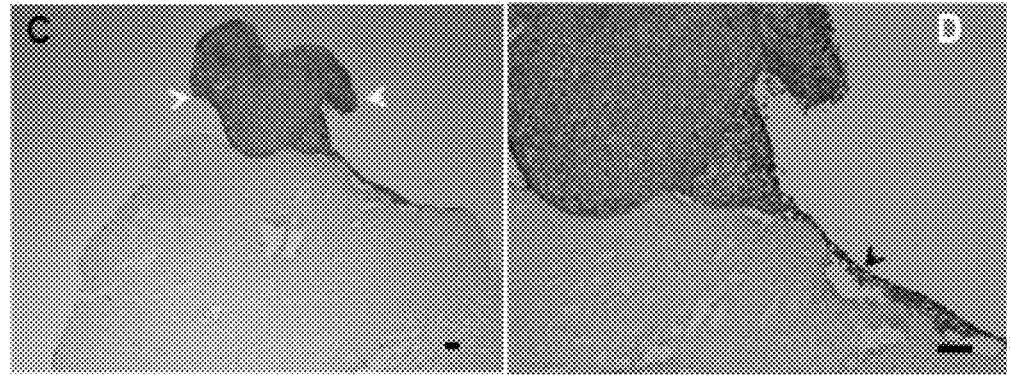
Figures 11E, 11F:
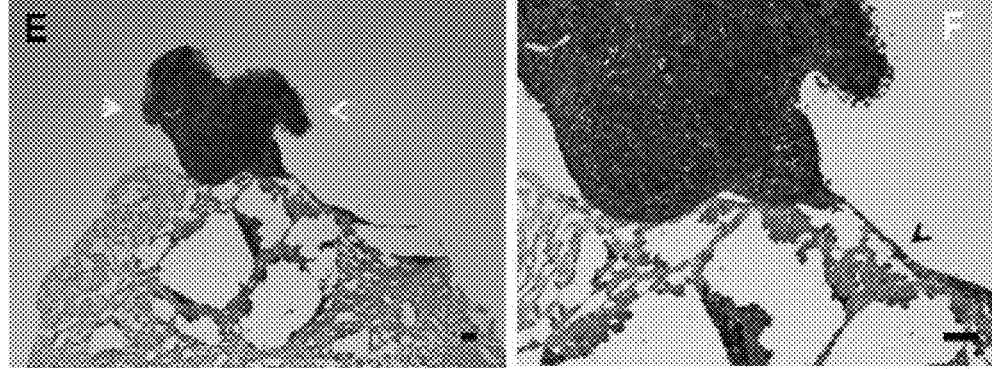

Shh staining on the other hand, identified three patterns of shh staining similar to versican staining patterns (see FIGS. 10A-10B). The first pattern is spindle-like cells that covered the area of cell condensation (see "a" in FIGS. 10A-10B), the second pattern is cuboidal cells with projections (see "b" in FIG. 10A-10B) that covered the sides of cell condensation areas and finally, cuboidal cells with abundant matrix in cell condensation areas (see "c" in FIGS. 10A-10B). An acellular matrix material (see white arrow in FIG. 10B) was seen in cell condensation area. This acellular material was pink in H&E stain and stained positive for shh. This material might represent keratin which appeared to have developed into more hair-like structures (see FIGS. 10C-10D). Similar staining pattern was observed with versican staining Additionally, pink staining extracellular material was identified (white arrow in FIG. 10B) in the area of cell condensation. This pink material might represent keratin. This keratinized material became more mature overtime and developed into hair-like structures (black arrows) seen in FIG. 10C and FIG. 10D. Scale bar is 100 microns.

Two days following their seeding on DWJM, WJMSCs formed a cellular clump that adhered to DWJM and the seeded cells appeared to have started to spread on the outer surface of DWJM (see FIGS. 11A-11D). This cellular clump was strongly positive for shh and versican. Following one week of osteogenic differentiation we recognized spindle-shaped cells on the outer DWJM surface and cuboidal cells in the area of cell condensation and both demonstrated strong Hedgehog staining. The same findings were appreciated week 4 of osteogenic differentiation presented earlier in FIGS. 9A-9C. Following their seeding on DWJM and prior to osteogenic differentiation, WJMSC demonstrated strong shh (see FIG. 11A and FIG. 11C) and versican (see FIG. 11B and FIG. 11D) expression by immunohistochemistry. WJMSCs developed cellular clumps with strong positivity for shh and versican (see FIG. 11A and FIG. 11B) and started to develop a thin layer, again positive for shh and versican (see FIG. 11C and FIG. 11D).

BMP-4 Secretion Decreases Over Time

It was found that BMP-4 secretion decreases over time despite expression by immunohistochemistry and Western blot. To determine the role of BMP-4 in hair follicle development in our model, we measured BMP-4 secretion by ELISA in culture supernatant over time. In these experiments, BMP-4 appeared to have gradually decreased to undetectable levels during the 4 week culture (data not shown). By the $4^{th}$ week, BMP-4 secretion was not detectable.

Figure 12:
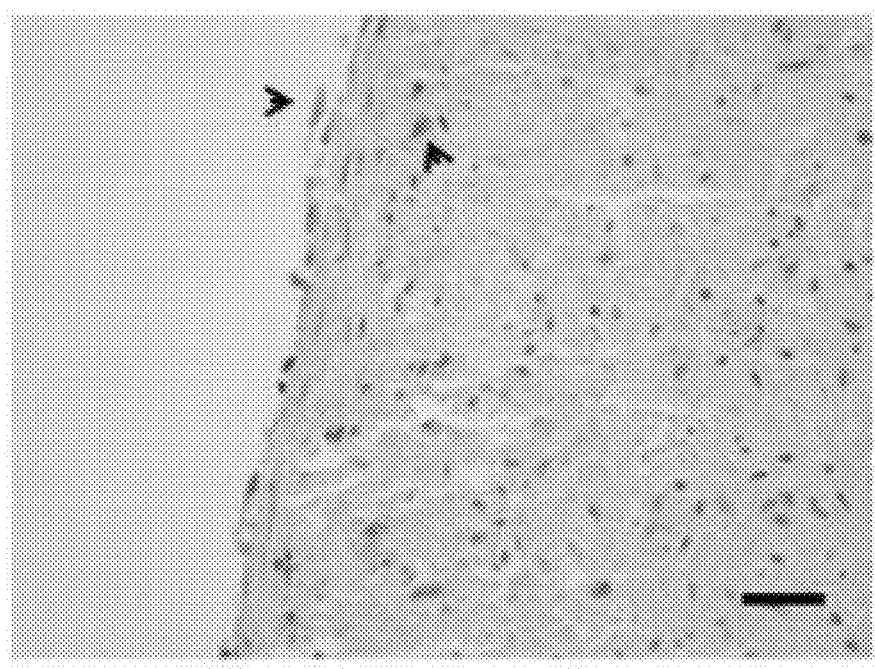
FIG. 12 includes an image that shows BMP-4 detection in DWJM by IHC.

On the other hand, BMP-4 was surprisingly detectable by IHC at the end of week 4 of osteogenic differentiation, though the staining was faint and sporadic (see FIG. 12). So, despite absence of BMP-4 in secreted form, BMP-4 was still detected inside the cells. According to literature, BMP-4 was thought to be expressed by the epithelium of the hair follicle and by dermal structures like dermal papilla. In our experiments, BMP-4 expression was detectable by IHC in the cell condensation area which we theorize was equivalent to dermal papilla and by the overlying spindle-like cells too, which we theorize were equivalent to hair epithelial placode. In FIG. 12, immunohistochemistry stained sections of the seeded DWJM demonstrated faintly positive BMP-4 staining in the surface cells and in the cell condensation area cells (black arrows).

Figure 13A:
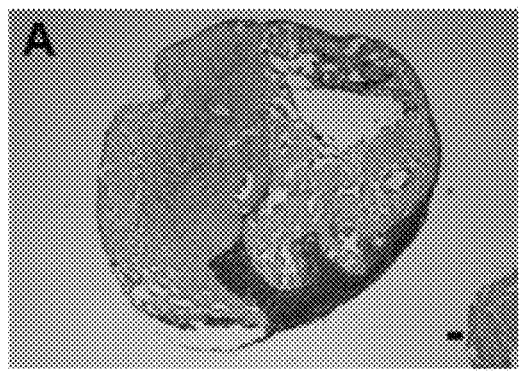
FIGS. 13A-13B include images that show tubular-like structures stained positive for versican.
Figure 13B:
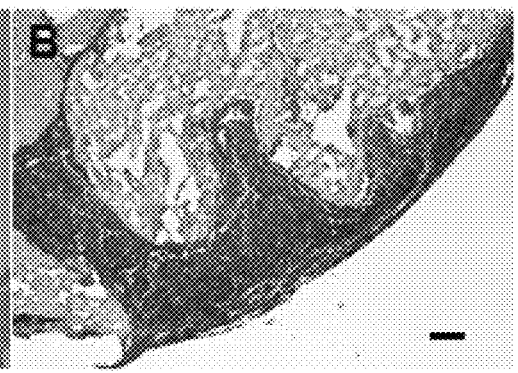
Figure 13C:
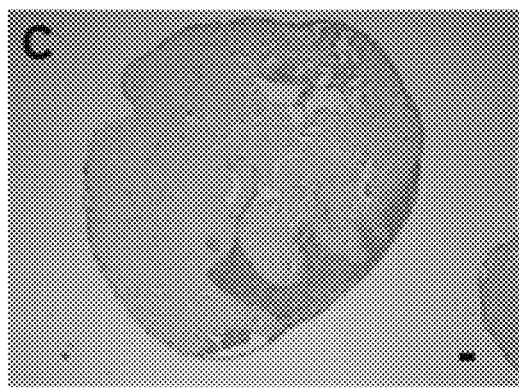
FIGS. 13C-13D include images that show tubular-like structures stained positive for shh.
Figure 13D:
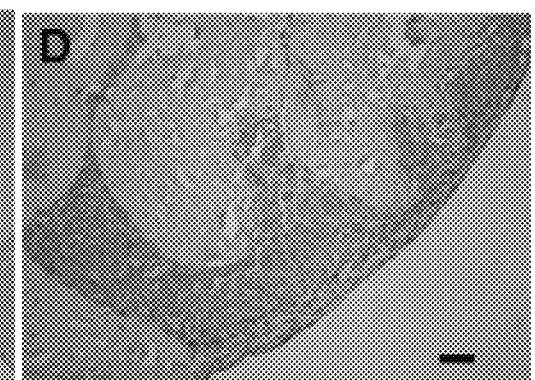

Additionally, BMP-4 was detected by Western blot though several slicing variants were potentially detected in our case (data not shown). According to National Center for Biotechnology Information (NCBI) Reference Sequence (RefSeq) data base, three variants of BMP-4 exist as a result of alternative splicing in the 5' untranslated region of BMP-4 gene. So, conceptually, several BMP-4 variants might have existed and could potentially explain our findings of more than one protein band. Western blot identified different bands at different time points with an approximately 85 KDa band recognized in control (week 0) and throughout osteogenic differentiation while bands with molecular weight less than 85 KDa were identified mainly after 2 and 4 weeks of osteogenic differentiation Cell Condensation Area Developing into Tubular Structures Dermal papilla cells were reported to develop structures that resemble tubules when cultured in a three-dimensional model of skin equivalent. Previously, dermal papilla cells were embedded in a collagen I matrix. In our model, tubular-like structures that stained positive for shh and versican were recognized to have developed in the area of cell condensation and invaded into the DWJM core (see FIGS. 13A-13D). Tubular structures were observed 2 weeks following osteogenic differentiation. These structures stained positive for versican in FIG. 13A and FIG. 13B and for shh in FIG. 13C and FIG. 13D. Scale bar 50 microns for FIG. 13A and FIG. 13C and 100 microns for FIG. 13B and FIG. 13D.

Experimental B—Osteogenic and Chondrogenic

Materials and Methods

Wharton's Jelly Mesenchymal Stromal Cell (WJMSC) Isolation

IRB approval was obtained for human umbilical cord collection and for the decellularization process and subsequent seeding and osteogenic and chondrogenic differentiation from the University of Kansas Medical Center (No. HSC 12129). In addition, IRB approval was obtained to use WJMSCs previously harvested for use in another study (No. HSC 11973). Umbilical cords were immediately collected after normal vaginal delivery and placed in a premade transfer solution and immediately refrigerated. Within 72 hours, the decellularization process was started.

Decellularization Process

Fresh human umbilical cords were transported from delivery room in physiologic saline containing amphotericin B, penicillin and streptomycin at 4° C. Under aseptic conditions in a biohood cabinet, pieces of fresh WJ matrix were aseptically dissected from the cord, separated from the blood vessels in pieces (approximately 5×30 mm) and decellularized in a custom apparatus. The decellularization process (patent pending) included multiple osmotic shock cycles using hypertonic and hypotonic solutions, a non-ionic detergent (Triton-X) and an anionic detergent (sodium lauroyl succinate) as well as an enzyme digestion with recombinant endonuclease (Benzonase™). All process residuals were removed with 36 hours of iterative solvent washouts (double deionized water and 40% ethyl alcohol) dialyzed against hydrophobic and ion exchange resin beads (IWT® TMD-8, Amberlite™ XAD16, Powex™ 550A Biobeads, all Sigma Aldrich). The decellularized matrix was then placed into a 10% protein and 10% DMSO solution and cryopreserved utilizing a computer controlled freezing profile that is material specific and designed to cool samples at 1° C. per minute. The DWJM was stored in a sterile environment until use at −180° C. to maintain bioactivity.

They were then subjected to two cycles of osmotic shock, alternating a hypertonic salt solution that included sodium chloride, mannitol, magnesium chloride, and KCl with an osmolarity of approximately 1,275 mOsm/L. This was alternated every hour with Triton X-100 0.05% in ddH$_2$O hourly at 5,000 rpm in centrifuge at 4° C. After two cycles of osmotic shock, the tissue was subjected to an anionic detergent (Sodium Lauroyl), sodium succinate (Sigma L5777), alternating with a recombinant nucleic acid enzyme, (Benzonase™) in buffered (Tris Hcl) water. These two steps required 16 hours, after which an organic solvent extraction with 40% ethyl alcohol was performed for 10 minutes at 5,000 rpm in the centrifuge at 4° C. All of the detergent and other processing residuals were then removed utilizing ion exchange beads in a reciprocating flow-through glass system for 30 hours at room temperature in ddH$_2$O. The ion exchange beads used were IWT-TMD (Sigma), XAD-16 Amberlite beads (Sigma), and Dowel Monosphere 550A UPW beads (Supelco). For cryopreservation, 10% protein albumin (Novozymes) and 10% DMSO (Sigma) solution were added and a material specific computer controlled freezing profile was utilized to freeze at −1° C./minute to −180° C.

DNA Quantification of DWJM

The DNA was isolated using DNeasy Blood and Tissue Kit from Qiagen (Duesseldorf, Germany) per manufacturer's instructions. PicoGreen dye (Molecular Probes, Eugene, Oreg.) was used and the extracted DNA was quantified fluorometrically using Quant-it dsDNA Kit HS from Invitrogen (Carlsbad, Calif.). The amount of extractable DNA was calculated per wet weight of tissue and expressed as a percent reduction in extractable DNA relative to nondecellularized tissues.

Mass Spectrometry

DWJM samples were snap-frozen using liquid nitrogen, homogenized using tissue homogenizer, and suspended in WJMSC culture medium. Prior to processing for mass spectrometry, DWJM samples were digested with trypsin and peptides were fractionated using high-performance liquid chromatography according to standard procedures. The protein pool extracted was denatured in 6M guanidine Hydrochloride, reduced, alkylated, and subsequently digested for 18 h with sequencing grade trypsin (Promega, 12 ng/L) at 37° C. Following enzymatic digestion, the extracted peptides were concentrated on a centrivac concentrator (Labconco) to a final volume of 50 µl. The peptide extracts were analyzed using a LTQ FT mass spectrometer (Thermo Fisher Scientific) coupled with a 2D NanoLC (Eksigent Technologies, California, USA). In each run, the sample was injected to a trap-column (100 µm ID fused silica, packed in-house with 3 cm of 100 Å, 5µ, Magic C18 particles, Michrom Bioresources) and washed with 0.1% formic acid for 15 minutes at 0.5 µl/min. For peptides elution the trap-column was coupled to an analytical column (75 µm ID fused silica, packed in-house with 9 cm of 100 Å, 5µ, Magic C18 particles, Michrom Bioresources) that was mounted on the electrospray stage of the mass spectrometer. The mobile phases A and B in the analytical run pump were 0.1% formic acid in water, and 0.1% formic acid in acetonitrile, respectively. The gradient profile was as follows: 0-5 min, 5-15% B; 5-190 min, 15-60% B; 190-200 min, 60 to 90% B; 200-205 min, 90% B. The flow rate was maintained at 300 nl/min and using an electrospray voltage of 1.9 kV with the ion transfer temperature set to 250° C. The mass spectrometer was controlled by the Xcalibur software to perform continuously mass scan analysis on the FT in the range of 400-1900 m/z at 50,000 resolution, followed by MSMS scans on the ion trap of the six most intense ions, with a dynamic exclusion of two repeat scans of the same ion, 30 s repeat duration and 90 sec exclusion duration. Normalized collision energy for MS/MS was set to 35%. For data analysis all MSMS scans were searched using Proteome Discoverer (version 5.3, Thermo Fisher). Database search was conducted against a human protein database derived from the NIBInr repository as in Jun. 1, 2011, using trypsin cleavage specificity, with a maximum of 2 missed cleavages. The following variable modifications were selected: oxidation of M, deamidation of N and Q. Carboxymethylation of C was selected as a fixed modification, and a maximum of 4 modifications/peptide. Estimation of false positive rate (FDR) was conducted by searching all spectra against a decoy database. For protein identification a FDR 1 (High confidence) or 5 (medium confidence) were defined as strict or relaxed. Amino acid sequence assignment of all peptides of interest was subsequently inspected manually.

Total Protein and Glycosaminoglycans (GAGs)

For total protein analysis, Pierce BCA protein assay kit (Thermo Scientific) was used applying the standard protocol according to manufacturer's recommendations. The Blyscan assay (Biocolor, UK) was used for analysis of sulfated proteoglycans according to the manufacturer's recommendations. Results were reported in µg/mg of glycosaminoglycan per wet tissue weight.

Preparation of DWJM for Seeding with WJMSCs

Figure 14A:
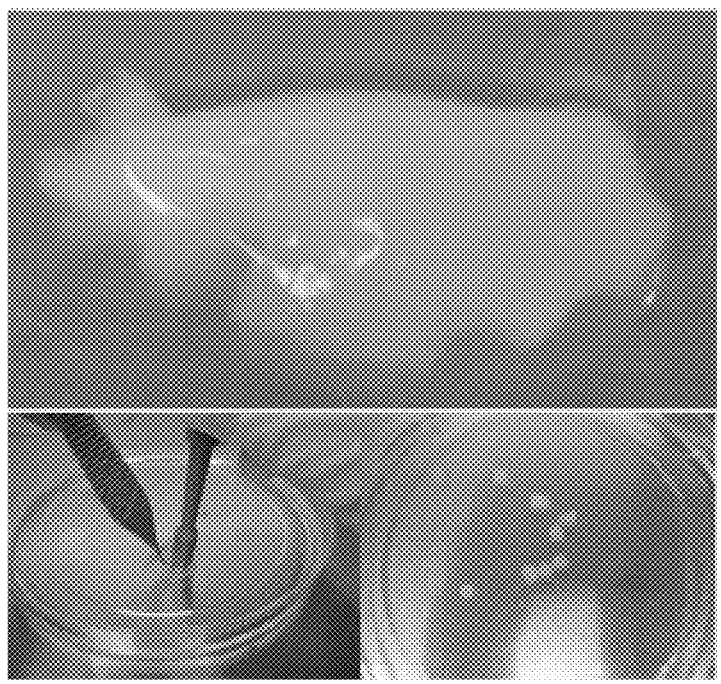
FIG. 14A includes images that show DWJM and fragments thereof.

Fresh fragments of DWJM obtained in transfer solution were placed in a refrigerator. The fragments were irregular in shape and size. Prior to seeding, the fragments were transferred under a laminar flow hood to a large Petri dish and covered with phosphate buffered saline (PBS). Pieces 5-7 mm in diameter were obtained using a sterile 5 mm or 7 mm skin punch biopsy kit (see FIG. 14A). The resulting DWJM pieces were cylindrical in shape with non-uniform heights, which varied between 2-3 mms. Accordingly, DWJM scaffolds' average volumes were 40-60 mL or 72 mm$^3$. From this point on, these pieces of DWJM will be referred to as DWJM scaffolds. To remove DWJM scaffolds from the punch biopsy kit, sterile forceps were used. The DWJM scaffolds were placed in a large Petri dish and washed with PBS twice. When the cells were ready to be seeded, the DWJM scaffolds were transferred to non-tissue culture treated plates.

Seeding DWJM Scaffolds with WJMSCs

Previously expanded and cryopreserved P7 WJMSCs from a single donor (gender was not documented) were thawed and plated on culture flasks. Expanded WJMSCs, up to the seventh passage, were suspended in culture medium of low-glucose DMEM with 10% fetal bovine serum (FBS), and 1% Penicillin and Streptomycin (Pen/Strep) all purchased from Life Technologies (Grand Island, N.Y.). After an additional passage, WJMSCs were trypsinized, collected in 50 ml conical tubes, centrifuged at 1500 rpm, and re-suspended in culture medium of low-glucose DMEM with 10% FBS and 1% Pen/Strep. $1 \times 10^6$ WJMSCs suspended in 50 µL culture medium seeded into each DWJM scaffold individually placed in each well of a 48-well plate followed by incubation on an orbital shaker at 50 rpm for 3 hours. The seeding density was $20 \times 10^6$/mL or $1.4 \times 10^4$/mm$^3$ DWJM scaffold. Following that, 0.5 ml of medium was added to each wells and the plate returned to the orbital shaker for 4 hours (plates were placed on the orbital shaker for a total of 7 hours). After that, another 0.5 ml of medium was added to the wells for a total of 1 ml of medium/well. Plates were put back into the incubator. After two days, the medium was changed to osteogenic medium (n=9) and chondrogenic medium (n=9). Appropriate controls were also used in case of osteogenic and chondrogenic differentiation for molecular testing, n=3 in each control set. DWJM scaffolds seeded with Wharton's jelly MSCs and cultured in culture medium for 2 or 6 weeks were used for 2 and 6 week controls, respectively. DWJM after MSC seeding and prior to differentiation were used for controls. Chondrogenic and osteogenic differentiation media were changed every other day for 4 weeks. Osteogenic medium consisted of culture medium (e.g., low glucose Dulbecco's Modified Eagle Medium (DMEM) with 10% FBS and 1% Pen/strep) supplemented by 100 nM dexamethasone (DEX; Sigma, St. Louis, Mo., USA), 5 mM β-glycerophosphate (B-GP; Sigma), 10 nM 1α,25-hydroxyvitamin D3 (VD3; Biomol International, Plymouth Meeting, Pa., USA) and 50 µg/ml ascorbic acid 2-phosphate (AA2P; Sigma). Chondrogenic medium consisted of DMEM high-glucose, TGF-β (10 ng/ml) (Peprotech), Pre-mix insulin-transferrin-selenium (ITS) (BD Biosciences), 50 ug/mL ascorbic acid (AA2P; Sigma), 1% Pen/Strep, 40 ug/mL L-proline, 100 uM sodium pyruvate, 0.1 uM dexamethasone (DEX; Sigma, St. Louis, Mo., USA), and 1% non-essential amino acid (NEAA). The experiments were done in triplicates for each time point and each culture condition.

Evaluating Seeded WJMSC Attachment to DWJM Scaffolds

To assess WJMSCs attachment to DWJM scaffolds, we seeded $1 \times 10^6$ WJMSCs on each DWJM scaffold in a 24-well culture plate. After 2 hours, the seeded DWJM scaffolds were transferred to a viewing chamber for confocal microscopy examination using Fluoview scanning laser confocal microscope (Olympus, Center Valley, Pa.). Prior to viewing, seeded DWJM scaffolds were rinsed with PBS twice and incubated with culture medium with 2 µg Calcein stain (Molecular Probes) added to each seeded DWJM scaffold. Calcein is a cell-permeant dye that in live cells is converted to green-fluorescent Calcein. We used this stain to track the seeded WJMSCs that remained alive in the DWJM scaffolds. Similarly, we viewed DWJM scaffolds seeded with WJMSCs and cultured in culture medium 24 and 48 hours following seeding.

Evaluating Seeded WJMSC Viability and Proliferation

To assess WJMSC viability and proliferative response to cell seeding on DWJM, we utilized alamarBlue (AB) assay (Biocentric). AB is a fluorometric assay that correlates with cell metabolic activity. We seeded DWJM scaffold pieces (7 mm in diameter and 2-3 mm in height) with expanded human Wharton's jelly mesenchymal stromal cells (WJMSCs). $1 \times 10^6$ cells were seeded on each DWJM scaffold. For controls, WJMSCs $1 \times 10^6$ were cultured as a monolayer in each well of a 24-well plate. AB was assessed 24 and 48 hours as well as 1 week following WJMSC seeding. The experiments were done in triplicates.

Seeding DWJM Scaffolds with MC3T3E1

Cryopreserved DWJM scaffolds provided in cryovials were thawed in water bath and under laminar flow hood placed in 12-well culture plate, washed with PBS twice and incubated in culture medium 24 hours in standard incubator. After incubation, the DWJM scaffolds (n=3), with variable shapes but approximately 60 mm$^3$ in volume, were washed with HEPES-buffered physiological salt solution (HPSS) once and then seeded with MC3T3E1, the seeding density was $80 \times 10^6$ cell/mL DWJM scaffold Initially, the cell suspension was added first and in 5 minutes, culture medium was added to a total of 1 ml/well. Medium was changed every other day and osteogenic differentiation medium was added on the fourth day till day 14. On day 14, the samples were processed for histological examination as discussed below.

Histology

For histology, three seeded DWJM scaffolds cultured in the chondrogenic medium and three seeded DWJM scaffolds grown in the osteogenic medium were placed in glass scintillation counter vials, 1 scaffold/vial. Scaffolds were covered with optimal cutting temperature (OTC) compound and placed in the 37° C. oven overnight. In the morning, vials were transferred to −20° C. freezer. In preparing the MC3T3E1 seeded DWJM scaffolds, a slightly different procedures was followed. The scaffolds were covered with OTC and immediately transferred to −20° C. freezer. Frozen sections, 5 µm in thickness, were used for histological analysis. Slides were reviewed using Olympus BX40 microscope and pictures were taken using DP72 digital camera.

Alizarin Red Staining Procedure

Five micron cryosections (5 µm) obtained from the osteogenic DWJM scaffolds were fixed in chilled 100% acetone for 2 minutes and rinsed in ultrapure water before staining Sections were stained with 2% Alizarin red stain, pH 4.1-4.3 (Sigma) for 3 min. Slides were blotted to remove excess dye, then dipped in 100% acetone 20 times, dipped in a 50:50 acetone/xylene solution, cleared in 100% xylene, then mounted in Permount.

Accustain Trichrome Staining Procedure

Slides containing cryosections were placed in −20° C. acetone for 2 minutes followed by MillQ water for additional 2 minutes. The slides were incubated in preheated Bouin's solution (56° C.) for 15 minutes and were transferred to a coupling jar containing tap water. The slides were rinsed with tap water to remove yellow stain, stained in Weigert's Iron Hematoxylin solution (Sigma) for 5 seconds and washed again with running tap water for 5 minutes. The slides were stained in Trichrome LG Stain solution (Sigma) for 5 minutes, followed by 0.5% acetic acid for 1 minute, and DiH20 for 1 minute. Finally, the slides were placed twice in 95% ethanol for 3 minutes each time and then 100% ethanol for same frequency and duration, and then dipped in Xylene and mounted with Permount.

Scanning Electron Microscopy (SEM)

DWJM scaffolds as well as osteogenic and chondrogenic DWJM were fixed in 2% glutaraldehyde for SEM processing. The fixed samples were washed with PBS for 10 minutes, placed into buffered 1% osmium tetroxide for 1 hour, and then washed 3 times 10 minutes each in distilled water. Following that, the samples were dehydrated through a graded series of ethanol from 30%, 70%, 80%, 95%, and 100% for 15 minutes each. Samples were then critical point dried in $CO_2$ in a model EMS 850 critical point dryer, following which they were mounted onto aluminum mounts and sputter coated with gold in a Pelco SC-6 sputter coater. Finally, samples were viewed using a Hitachi S-2700 scanning electron microscope.

Transmission Electron Microscopy (TEM)

For TEM, scaffolds were rinsed in buffer prior to fixing in 1% to 2% osmium tetroxide for 1 hour. After osmication, the scaffolds were dehydrated for 10-15 minutes in 30%, 70%, 80%, 95%, and 100% ethanol series before placing them in propylene oxide (PO) for 10 minutes twice. The scaffolds were then placed in equal mix of resin and PO overnight to allow tissue infiltration. At this point, the half/half mix was removed from the tissue and fresh 100% resin mixture was added to the sample and was allowed to sit on a platform rocker for at least 30 min. Following that, the samples were placed in a mold and positioned as needed, and resin was added to fill-out the mold. Finally, the samples were placed in 60° C. oven overnight to cure the resin. Samples were then sectioned using a Leica UCT ultramicrotome at 80 nm in thickness and contrasted with 4% uranyl acetate and Sato's Lead Citrate. The samples were viewed at 80 KV with a JEOL JEM-1400 TEM.

Tissue samples (25 mg) were crushed over liquid nitrogen and digested with a detergent solution and proteinase K at 50° C. for 3 hours. The DNA was separated from contaminating proteins and lipids by adding sodium perchlorate, chloroform and nucleon resin (Amersham Biosciences). The extracted DNA was precipitated with cold ethanol, centrifuged into a pellet, and resuspended in buffer. PicoGreen dye (Molecular Probes, Eugene, Oreg.) was added to the resuspended pellet and the extractable DNA quantified fluorometrically. The amount of extractable DNA was calculated per wet weight of tissue and expressed as a percent reduction in extractable DNA relative to nondecellularized tissues.

RNA Isolation and RT-PCR

Recellularized DWJM matrices (n=4) were processed prior to osteogenic or chondrogenic differentiation as controls. On the other hand, recellularized DWJM that underwent osteogenic or chondrogenic differentiation was processed at two time points, 2 and 4 weeks. Four samples were processed for each time point. The following markers were assessed: runt-related transcription factor 2 (RUNX2), osteocalcin (OCN), and collagen type I (COL 1) for osteogenic differentiation and sex determining region Y-box 9 (SOX-9), aggrecan, and collagen type 2 (COL 2) for chondrogenic differentiation. Recellularized scaffolds undergoing chondrogenic or osteogenic differentiation were homogenized using a tissue homogenizer. Total RNA was extracted from cells using 1.5 ml Trizol reagent (Invitrogen) following the manufacturer's instructions. Total RNA concentration and purity was determined using spectrophotometer (nanodrop; Wilmington, Del., USA). The mRNA samples were converted to cDNA using a high-capacity cDNA archive kit (Applied Biosystems, Foster City, Calif., USA) following supplier's instructions. TaqMan gene expression assay kits (Applied Biosystems) were used for transcript levels of COL1, RUNX2, OCN, SOX-9, aggrecan, and COL2 using a real-time reverse transcriptase polymerase chain reaction (RT-PCR) in an Applied Biosystems 7500 system. A $2^{-\Delta\Delta Ct}$ method was used to evaluate the relative mRNA expression level for each target gene in 2 and 4 week osteogenic and chondrogenic DWJM matrices. $\Delta Ct$ values were obtained by the difference between the Ct values of target genes and the glyceraldehyde 3-phosphate dehydrogenase (GAPDH) gene. They were then normalized by subtracting the $\Delta Ct$ value of the calibrator sample, their respective Ct values in the 0 week osteogenic, or chondrogenic DWJM normalized to 1, to obtain $\Delta\Delta Ct$ values.

Mechanical Testing

Recellularized DWJM scaffolds undergoing osteogenic differentiation or chondrogenic differentiation were evaluated for biomechanical properties. DWJM (acellular) was used as a control. Samples were placed on a glass slide and the diameter was measured with micrometer under a stereomicroscope. Samples were then loaded in an RSA-III dynamic mechanical analyzer (TA Instruments) and tested under unconfined uniaxial compression. Matrix height was measured directly using the RSA-III. A stress versus strain curve was generated by compressing each sample at a rate of 0.005 mm/s.

Statistical Analysis

All data were expressed as means±one standard deviation (SD) and analyzed using Student's t-tests. Statistical significance was determined by a statistical threshold of $p<0.05$.

Results

Successful Decellularization of Wharton's Jelly Matrix (WJM)

Figure 14B:
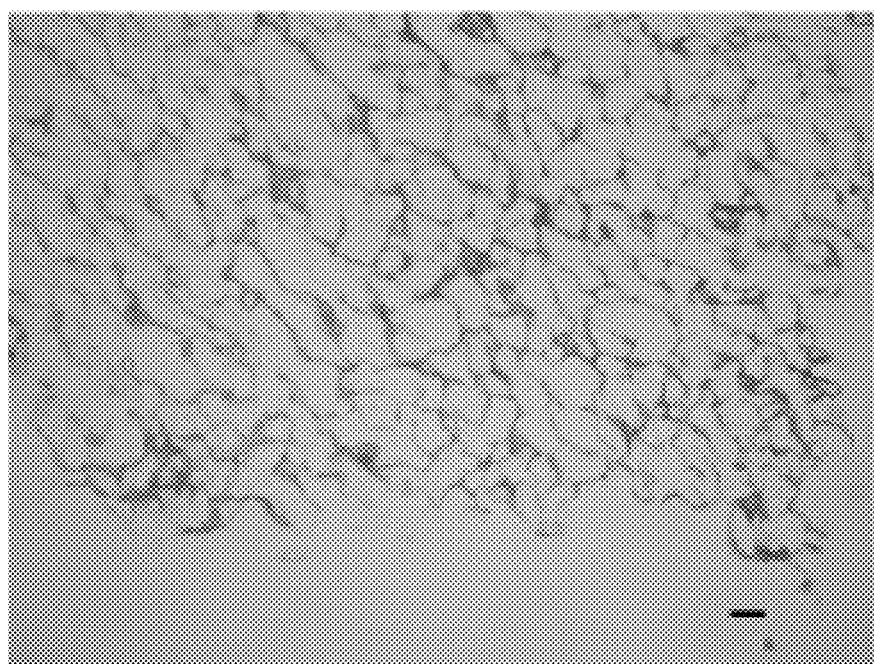
FIG. 14B includes an image that shows DWJM devoid of cellular components.

The isolated and DWJM was examined for successful decellularization using the following described methods. Examination of histology sections of the DWJM with H&E staining of the decellularized matrix that revealed matrix material devoid of cellular elements (see FIG. 14B), where empty spaces within the DWJM were observed (Scale bar represents 0.1 mm).

Figure 14C:
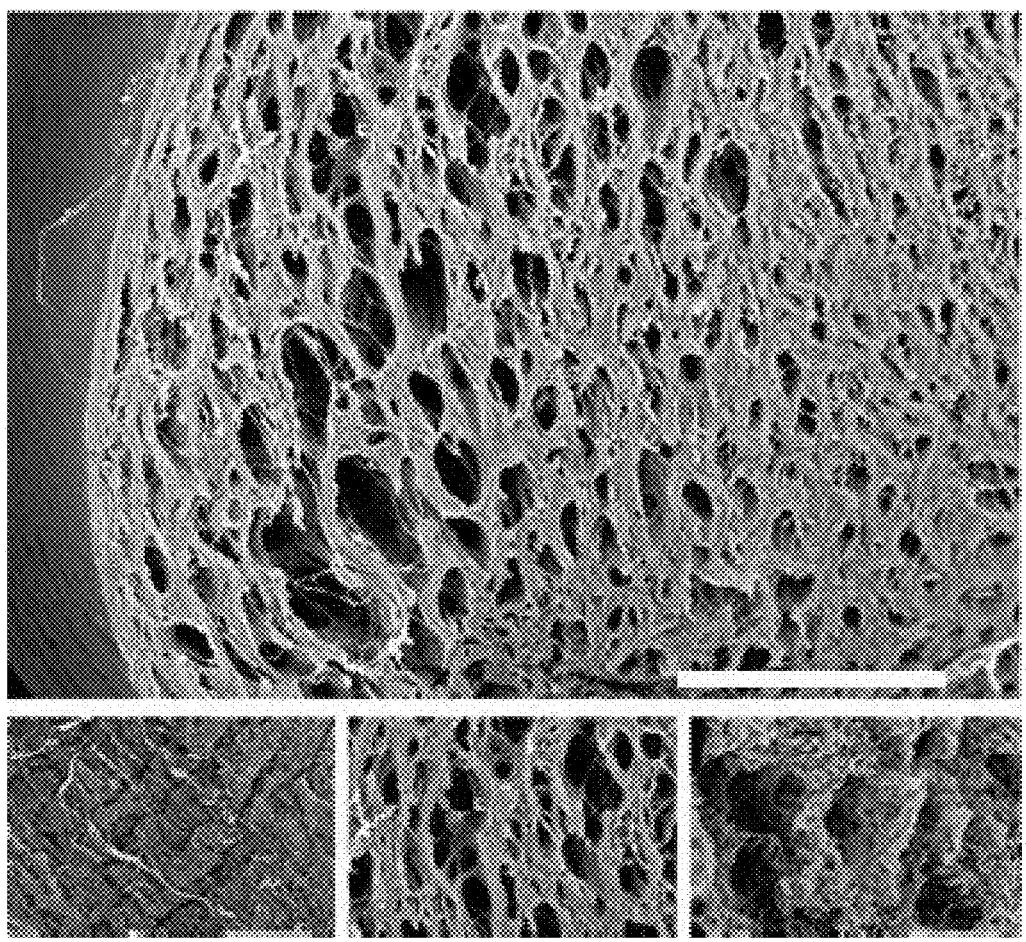
FIG. 14C includes images that show scanning electron microscopy of DWJM.

Scanning electron microscopy pictures of DWJM identified areas with different structures (see FIG. 14C). One surface appeared flat with compact matrix (left lower image of FIG. 14C). On the other hand, less dense tissue with open spaces was identified in other areas (lower middle and right lower images of FIG. 14C). Some spaces were larger (lower middle image of FIG. 14C) than others (right lower image of FIG. 14C). Scale bar for the full top picture was 600 µm.

Figure 14D:
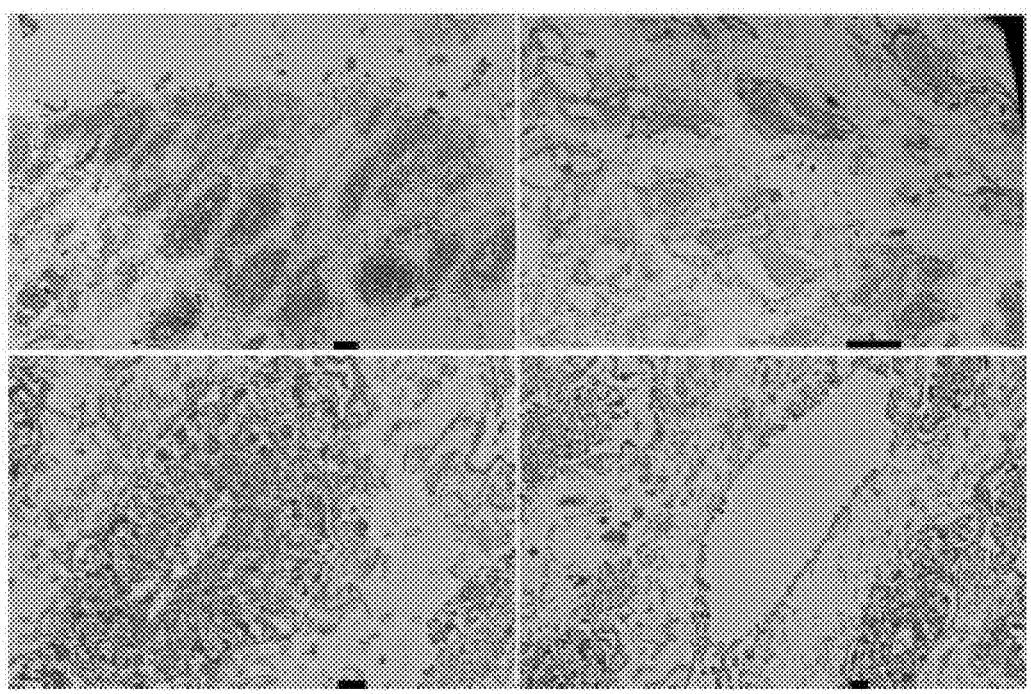
FIG. 14D includes images that show transition electron microscopy of DWJM devoid of cells.

Transition electron microscopy showed absence of cells in the DWJM, on the other hand, it revealed extracellular matrix (see FIG. 14D). FIG. 14D represents transmission electron microscopy pictures of DWJM. More dense areas of DWJM (left upper image of FIG. 14D) and less dense areas (right upper image of FIG. 14D) were observed. The open spaces were occupied in some areas (left lower image of FIG. 14D) and empty in others (right lower image of FIG. 14D). No occupying cells were observed in all panels.

DNA Quantification

Random DWJM samples were run in triplicates to determine DNA content and random samples from original WJ tissue were used for comparison. The average dsDNA per DWJM sample wet weight was 0.0017 µg/mg (range: 0.0014-0.002 µg/mg) with standard deviation of 0.0002 µg/mg and the average dsDNA per WJ matrix wet weight sample was 0.051 µg/mg (range: 0.0317-0.0733 µg/mg) with standard deviation of 0.019 µg/mg. The average percent dsDNA removal was 96.6% with standard deviation of 0.4%. Based on these results, we believe that the decellularization process yielded a matrix material with variable pore sizes that is devoid of cells or cellular elements.

WJMSCs Seeded on DWJM

Figure 15A:
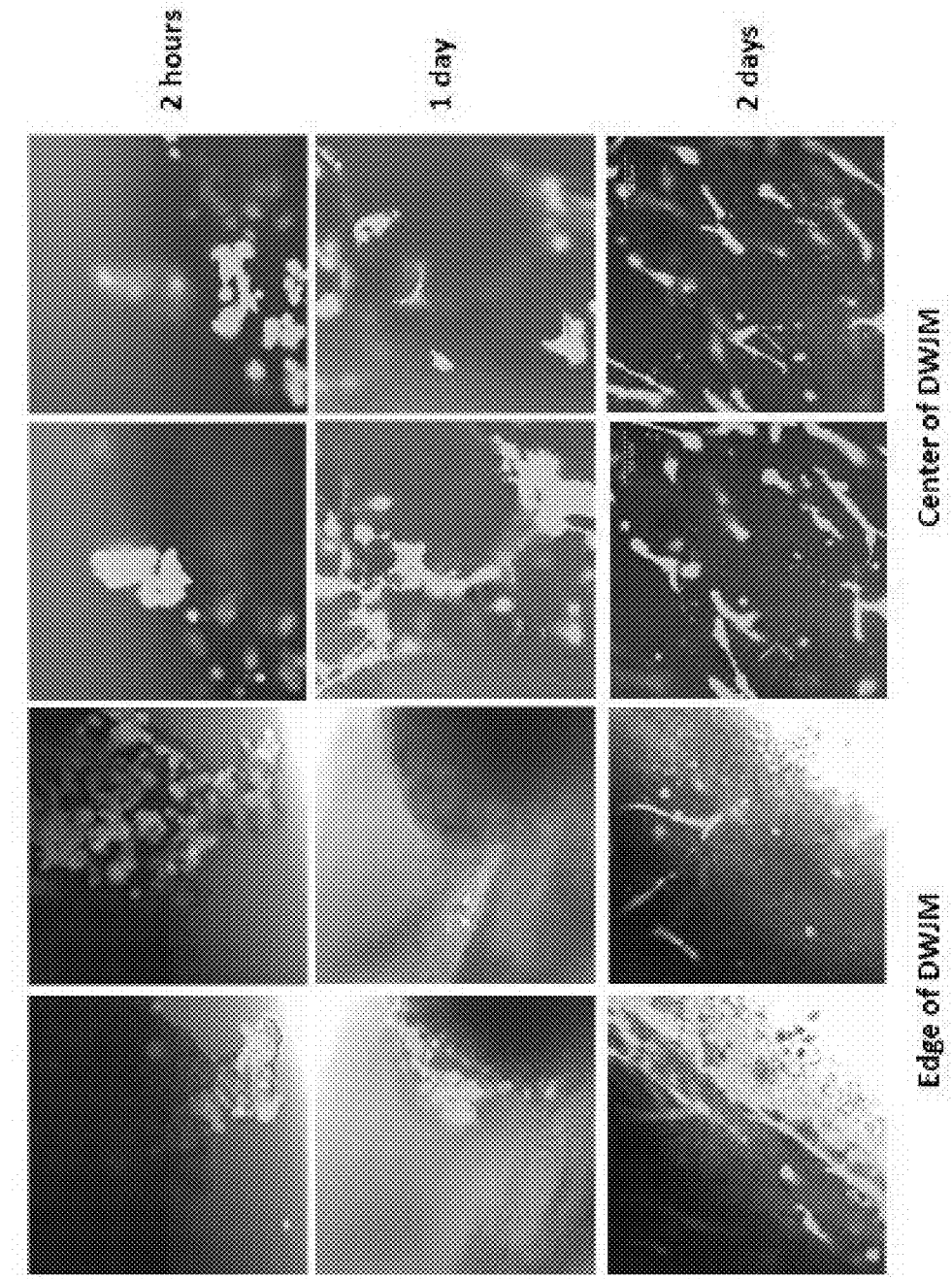
FIG. 15A includes confocal microscopy images showing adherence of WJMSCs to DWJM scaffold material following their seeding.

It was found that WJMSCs seeded on DWJM scaffolds immediately attach to DWJM scaffolds and penetrate deeper into DWJM scaffolds. In these experiments, we utilized Calcein stain to track WJMSCs after they were seeded on DWJM. Within 2 hours of seeding, WJMSCs were noticed to form clusters of round cells that firmly attached to the surface of DWJM scaffolds (FIG. 15A). Additionally, WJMSCs with rounded cell morphology were noticed to penetrate deeper into DWJM scaffolds. Over the next two days, WJMSCs were noticed to penetrate deeper and in a uniform way inside DWJM scaffolds. They also appeared to be less rounded and to have acquired a spindle-shaped appearance. On the other hand, WJMSCs continued to form clusters on the surface of DWJM scaffolds in some areas. Collectively, these studies confirm that WJMSCs attached firmly to DWJM scaffolds, penetrated deeper into DWJM scaffolds, distributed in a uniform fashion and remained alive inside DWJM scaffolds, and in some cases formed WJMSC clusters attached to the surface of DWJM scaffolds.

FIG. 15A shows confocal microscopy images demonstrating adherence of Wharton's jelly mesenchymal stromal cells (WJMSCs) to DWJM scaffold material following their seeding. Upper panels represent confocal microscopy pictures demonstrating WJMSC's attachment to DWJM scaffold within 2 hours, middle panels represent WJMSC attachment to DWJM scaffold following 1 day, and lower panels represent WJMSC attachment to DWJM scaffold following 2 days of seeding. Prior to imaging, seeded DWJM scaffolds were transferred to viewing chamber and rinsed with phosphate buffer saline twice. Calcein stain was then added to allow for imaging of intact cells which demonstrated green fluorescence. The left two panels demonstrate WJMSC attachment to—and penetration of a random edge of a DWJM scaffold while the right two panels demonstrate WJMSC attachment to—and penetration of the center of a DWJM. Within two hours of seeding, WJMSCs formed a clump of cells upon attachment to DWJM edge and penetrated into deeper parts of DWJM as single cells. Similar findings were seen in DWJM center within the first two hours of seeding. On day 1 post-seeding, WJMSCs continued to form cell clumps on one of DWJM edges, while individual spindle-like cells were seen spreading on surface. On day 1, WJMSCs also penetrated deeper into DWJM center and started to form processes and acquire a spindle-like shape. Two days post-seeding, WJMSCs continued to cluster on the surface of a DWJM edge while assuming a spindle-like shape in deeper parts of DWJM edge. On the other hand, WJMSCs assumed a spindle-like shape when a DWJM center was examined. Scale bar represents 100 µm.

Seeded WJMSCs Viability and Proliferation

To determine the impact of DWJM scaffolds on proliferative response of seeded WJMSCs, we utilized alamarBlue assay. In these experiments, WJMSCs seeded on DWJM scaffolds or cultured as a monolayer continued to proliferate overtime evident by significant increase in fluorescence over one week of culture (see FIG. 15B). Overall, the fluorescence values were significantly higher in WJMSCs cultured in monolayer than WJMSCs cultured in DWJM scaffolds. We speculate that the difference in fluorescence reflects differences in the tempo of proliferation between cells cultured in three dimensions (3D) versus 2 dimensions (2D). Cells cultured in 3D spend more time to penetrate deeper into DWJM scaffolds and potentially use part of their cellular energy to do so. On the other hand, cells cultured in 2D grow horizontally until they become confluent and then they form clusters of round cells (personal observation). Similarly, other studies have shown that 3D culture conditions were superior to 2D conditions in maintaining original spindle-shape morphology. (Wang et al., 2006) The impact of culture condition (2D versus 3D) on cell proliferation has been examined previously. In some studies, 3D culture conditions were found to slow down cell proliferation. (Scaglione et al., 2006) These findings confirm that DWJM supported WJMSCs proliferation; however, it altered the tempo of their proliferation reflective of 3D culture environment.

Figure 15B:
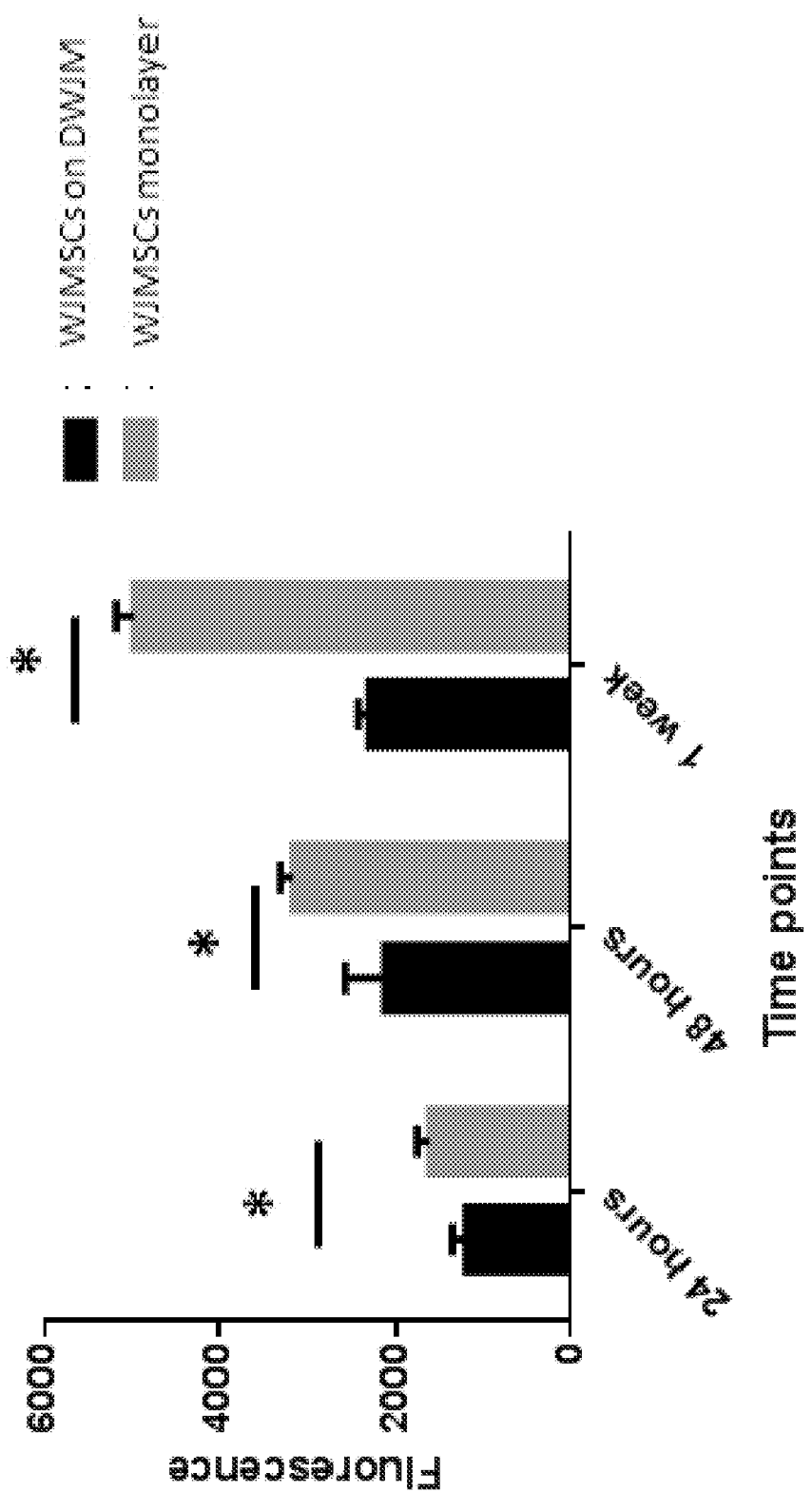
FIG. 15B includes a graph that represents WJMSC proliferation measured by alamarBlue assay following seeding on DWJM scaffolds.

FIG. 15B includes a graph that represents WJMSC proliferation measured by alamarBlue assay following seeding on DWJM scaffolds. WJMSCs were either seeded on DWJM scaffolds or were allowed to adhere to culture wells as a monolayer (control). The proliferation of WJMSCs seeded on DWJM scaffolds increased over time evidenced by significant increase in fluorescence over time. Similarly, WJMSCs cultured as a monolayer demonstrated increased proliferation over time as evidenced by significant increase in fluorescence over the same time points. However, significantly higher proliferation measured by fluorescence was demonstrated by WJMSCs growing as a monolayer compared to WJMSCs seeded onto DWJM. * indicate statistical significance ($p<0.05$)

Induction of Osteogenic or Chondrogenic Differentiation

Seeding of DWJM was followed closely using Nikon Inverted Eclipse TS100 phase-contrast microscope. The day following their seeding, WJMSCs were shown to be clearly invading the DWJM scaffold in waves. Some areas of the DWJM seemed to attract the WJMSCs more effectively than other areas.

Osteogenic Differentiation
SEM and TEM Pictures

After 4 weeks of exposure to osteogenic differentiation medium, osteogenic scaffolds were examined by SEM and TEM and compared to DWJM. SEM examination of the osteogenic DWJM clearly demonstrated absence of empty lacunae. The latter were occupied by cells and cell products. TEM examination demonstrated that the majority of the seeded and differentiated cells occupied the surface areas of the DWJM. Deeper areas of DWJM showed areas of transition where disintegrating cells were seen close to matrix proteins. Finally, the deepest part of the osteogenic DWJM, revealed matrix proteins with collagen fibrils and absence of intact cells.

Histology Sections

In histology sections stained with Alizarin red we demonstrate red staining consistent with positive mineral deposition Chondrogenic Differentiation
SEM and TEM Pictures After 4 weeks of exposure to chondrogenic differentiation medium, chondrogenic DWJM scaffolds were examined by SEM and TEM and compared to DWJM. SEM examination of the chondrogenic DWJM clearly demonstrated absence of empty lacunae. The latter were occupied by cells and cell products. TEM examination demonstrated that the majority of the seeded and differentiated cells occupied the surface areas of the DWJM. Deeper areas of DWJM showed areas of transition were disintegrating cells were seen close to matrix proteins. Finally, the deepest part of the chondrogenic DWJM, revealed matrix material and absence of intact cells.

Histology Sections

In histology sections stained with Trichrome stain we noticed areas of red stain indicative of active cellular elements and blue areas indicative of collagen matrix. We noticed more intense staining in some areas of the DWJM, which could be related to the orientation of the seeded surface. On the other hand, interstitially located red stained areas were noted within the blue staining areas.

Seeding DWJM with MC3T3E1

Immediate attachment occurred within 25 minutes, where MC3T3E1 cells were noticed to have attached to DWJM.

Histology Sections

In histology sections stained with H&E, MC3T3E1 cells were noticed to occupy DWJM outer aspect of DWJM and in areas the deep part of the matrix. Alizarin red stain indicates areas of calcium mineralization within the seeded matrix.

DWJM Scaffold Composition

Next, we examined the various components of DWJM utilizing mass spectrometry. Mass spectrometry analysis identified several proteins in DWJM, notably, collagen I, III, VI, and XII. In addition, matrix proteins like fibronectin I, tenascin and lumican were identified. Transforming growth factor, beta-induced (TGFBI) was also identified. A list of the proteins identified on mass spectrometry evaluation of DWJM is described in Table-1. Additionally, we performed a BCA and GAG analyses. BCA analysis revealed no soluble proteins, which is somehow expected following successful decellularization. We speculate that the discrepancy between mass spectrometry results that identified many proteins and BCA analysis results that did not reveal any soluble proteins is related to the differences in the sensitivity of the detection method. To further explain, BCA measures total soluble proteins based on the copper ion bonding with the peptide bonds. Depending on the extent and degree of splitting of these protein-protein bonds, BCA assay might not identify some peptide fragments. On the other hand, mass spectrometry will identify these peptide fragments. Similar discrepancy between mass spectrometry results and other protein detection methods like histology or immunohistochemistry have been described. (Welham et al., 2013) On the other hand, GAG analysis did show that DWJM contained sulfated GAGs at an average of 0.661 ug/mg (standard deviation=0.09).

Electron Microscopy

After 4 weeks of exposure to osteogenic differentiation medium, osteogenic DWJM scaffolds were examined by SEM and TEM (see FIG. 16A) and compared to DWJM scaffolds prior to seeding (see FIGS. 14C and 14D). SEM examination of the osteogenic DWJM scaffolds clearly demonstrated absence of empty spaces seen in DWJM scaffolds prior to seeding (see FIG. 16A). In osteogenic DWJM scaffolds, these empty spaces were occupied by cells and cell products. TEM examination demonstrated that the majority of the intact cells occupied the surface areas of DWJM scaffolds (see FIG. 16B). Deeper parts of DWJM scaffolds, on the other hand, demonstrated areas of transition where disintegrating cells were seen close to matrix proteins (see FIG. 16B). As an explanation for this finding, we hypothesized that these cells must have undergone cellular changes or possibly apoptosis when surrounded with matrix material. Indeed, bone osteoblasts either become osteocytes or undergo apoptosis when become surrounded with matrix material. (Dallas and Bonewald, 2010; Manolagas, 2000) Finally, the deepest part of the osteogenic DWJM scaffolds revealed matrix proteins with collagen fibrils and an absence of intact cells.

Figure 16A:
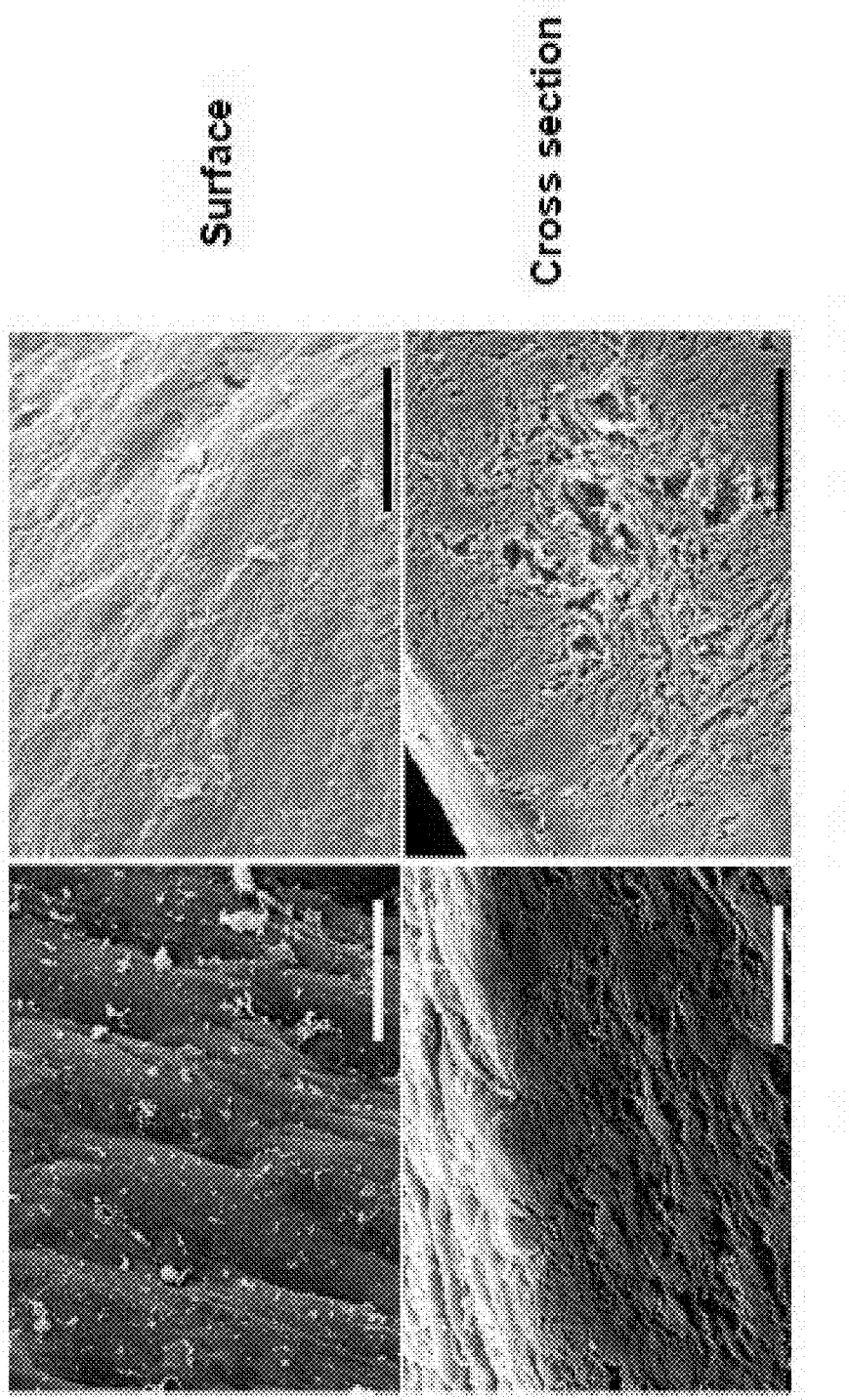
FIG. 16A includes images that show osteogenic and chondrogenic differentiation for surface and cross-sections of the DWJM having WJMSCs.

In FIG. 16A, upper images represent scanning electron microscopy (SEM) images of DWJM scaffold surface following osteogenic differentiation (upper left) or chondrogenic differentiation (upper right). The surface appears smooth which is different from DWJM surface prior to seeding and differentiation. In FIG. 16A, lower images represent SEM images of a cross section of a seeded DWJM scaffold after osteogenic differentiation (lower left) or chondrogenic differentiation (lower right). In these images there are no empty spaces compared to DWJM scaffold prior to seeding.

Figure 16B:
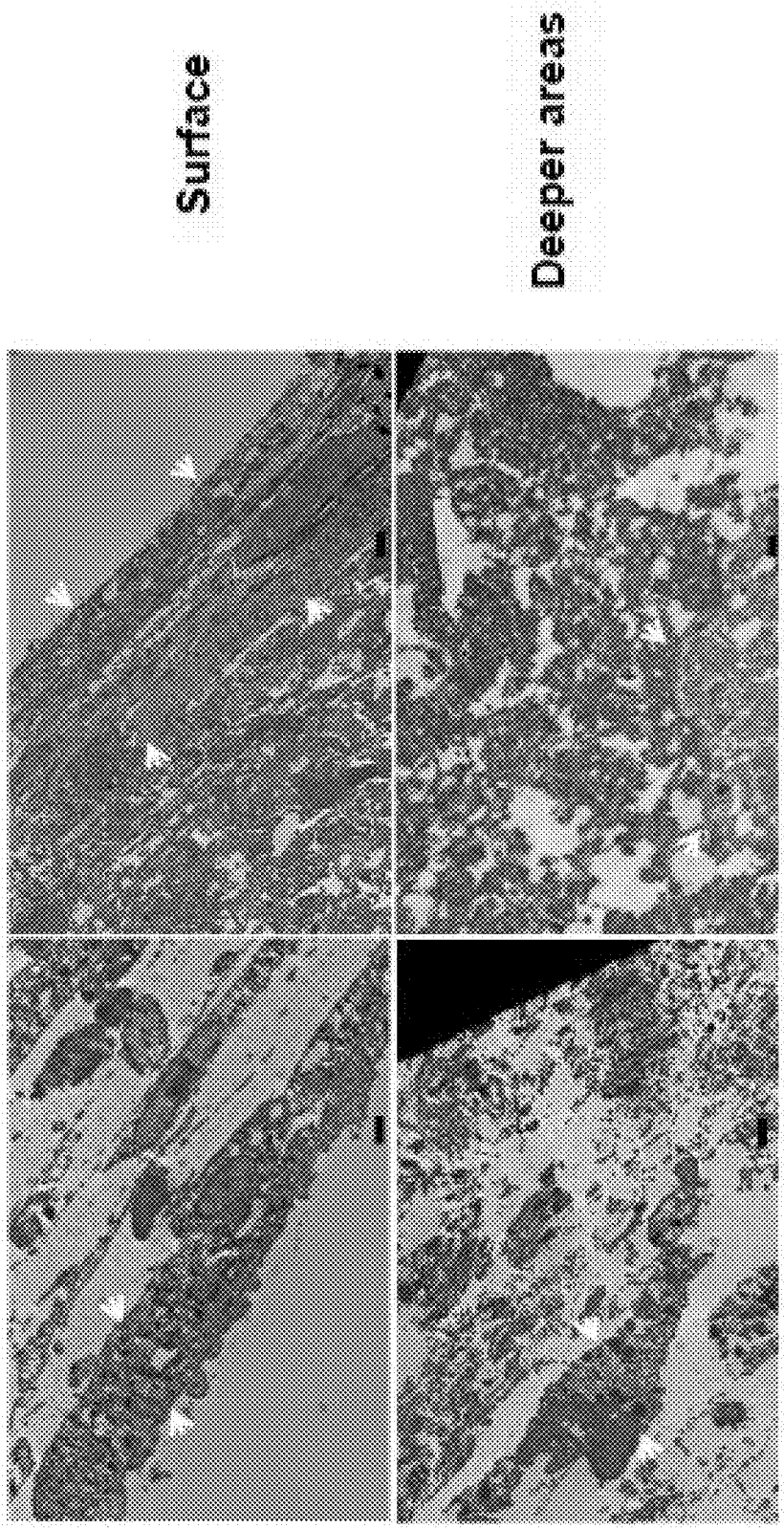
FIG. 16B includes images that show osteogenic and chondrogenic differentiation for surface and deeper cross-sections of the DWJM having WJMSCs.

In FIG. 16B, upper images represent transmission electron microscopy (TEM) images of surface layers of DWJM following seeding and differentiation. A thin layer of surface cells (white arrows) in osteogenic differentiated DWJM scaffold (left upper) or chondrogenic differentiated DWJM scaffold (right upper) is demonstrated. In FIG. 16B, lower images represent TEM images of deeper parts of DWJM scaffold in which there is an evidence of cell disintegration (white arrows) seen in close proximity to a matrix material in both osteogenic and chondrogenic differentiated DWJM (Scale bar represents 231 µm in panel A-upper images, 43 µm in panel A-left lower image, 150 µm in panel A-right lower image, and 2 µm in all panel B images except the scale bar in the panel B-right lower image which represents 500 nm).

Histology

Figure 17A:
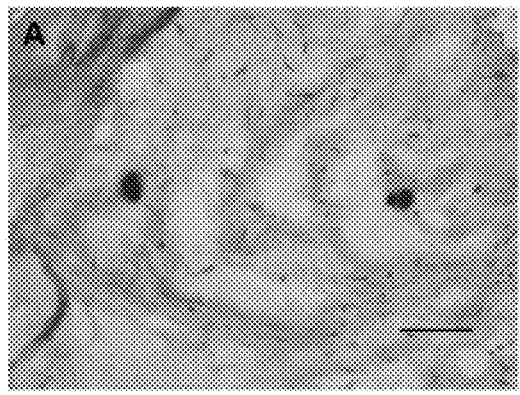
FIGS. 17A-17B includes images that show alizarin red stained sections showing mineral deposition in osteogenic DWJM.
Figure 17B:
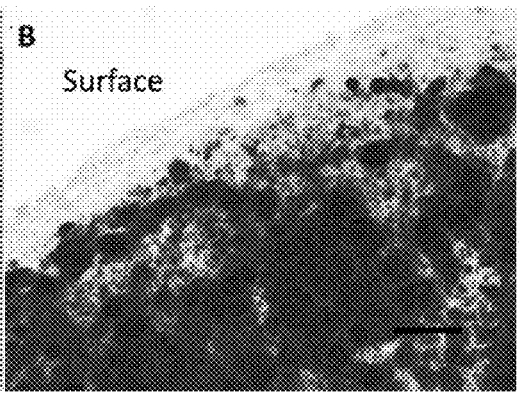

Alizarin red stained sections demonstrated areas of red staining consistent with positive mineral deposition in osteogenic DWJM scaffolds (see FIG. 17A). However, the intensity of red staining was higher and the distribution of staining was more uniform following 6 weeks of osteogenic differentiation (see FIG. 17B). Microscopy images of FIG. 17A and FIG. 17B in DWJM represent Alizarin red stained sections of an osteogenic differentiated DWJM. In FIG. 17A in DWJM, few areas of intense red staining are demonstrated after 4 weeks of osteogenic differentiation. In contrast, the image in FIG. 17B of DWJM demonstrates intense red staining evident after 6 weeks of osteogenic differentiation. Areas of red staining represent calcium mineralization (Scale bar represents 0.06 mm).

Figure 17C:
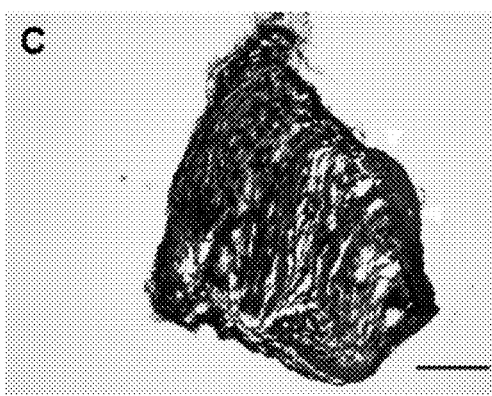
FIG. 17C-17D include images that show trichrome stained sections showing condrogenic areas indicative of collagen matrix.
Figure 17D:
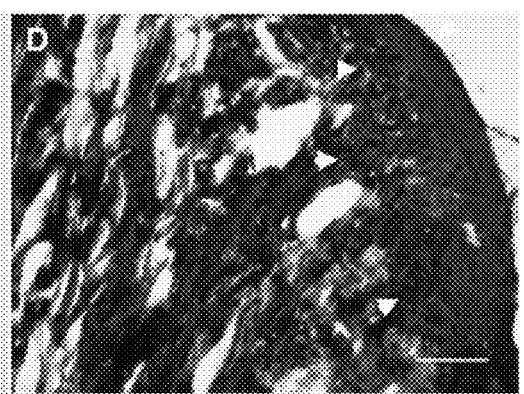

In the case of chondrogenic DWJM scaffolds, trichrome stained sections demonstrated areas of blue staining indicative of collagen matrix (see FIGS. 17C-17D). Red staining was noticed between areas of blue staining and in predominantly surface areas. These areas of red staining might be related to cytoplasmic staining and the predominantly red staining surface area might reflect condensation of seeded WJMSCs. Microscopy images in FIG. 17C and FIG. 17D of DWJM represent trichrome stained sections of a chondrogenic differentiated DWJM. Areas of dense blue staining are demonstrated. Between areas of blue staining red staining cells are observed. The red stain clearly condenses (white arrows) in one area of DWJM scaffold. While blue staining corresponds to collagen matrix, red staining might reflect the cytoplasm of WJMSCs. Chondrogenic differentiation, accordingly, might have occurred in an asymmetrical fashion. (Scale bar represented 0.25 mm in FIG. 4C and 0.06 mm in FIG. 17D).

Molecular Tests

Figure 18A:
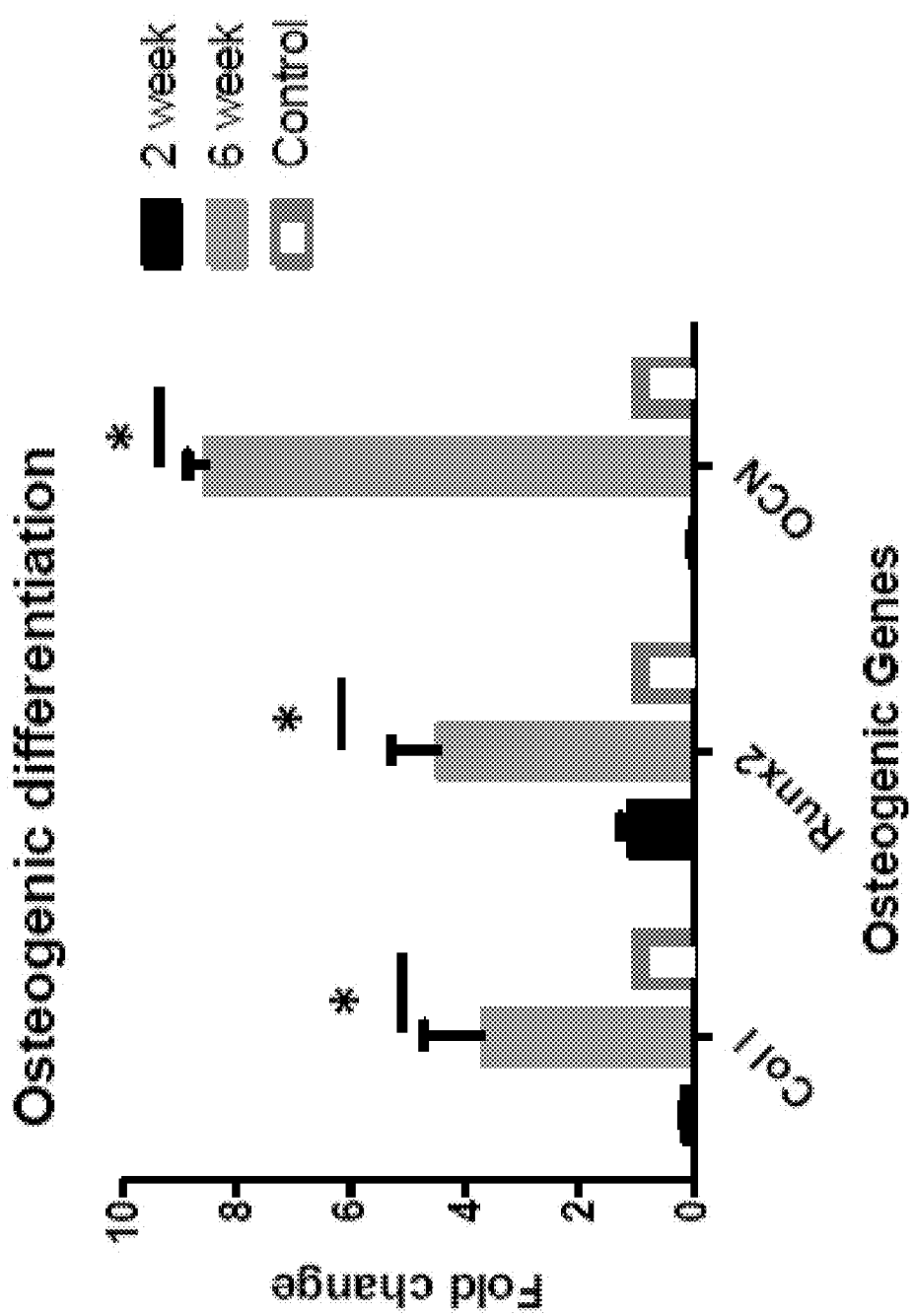
FIG. 18A includes a graph that shows osteogenic differentiation for osteogenic genes at 2 and 6 weeks.
Figure 18B:
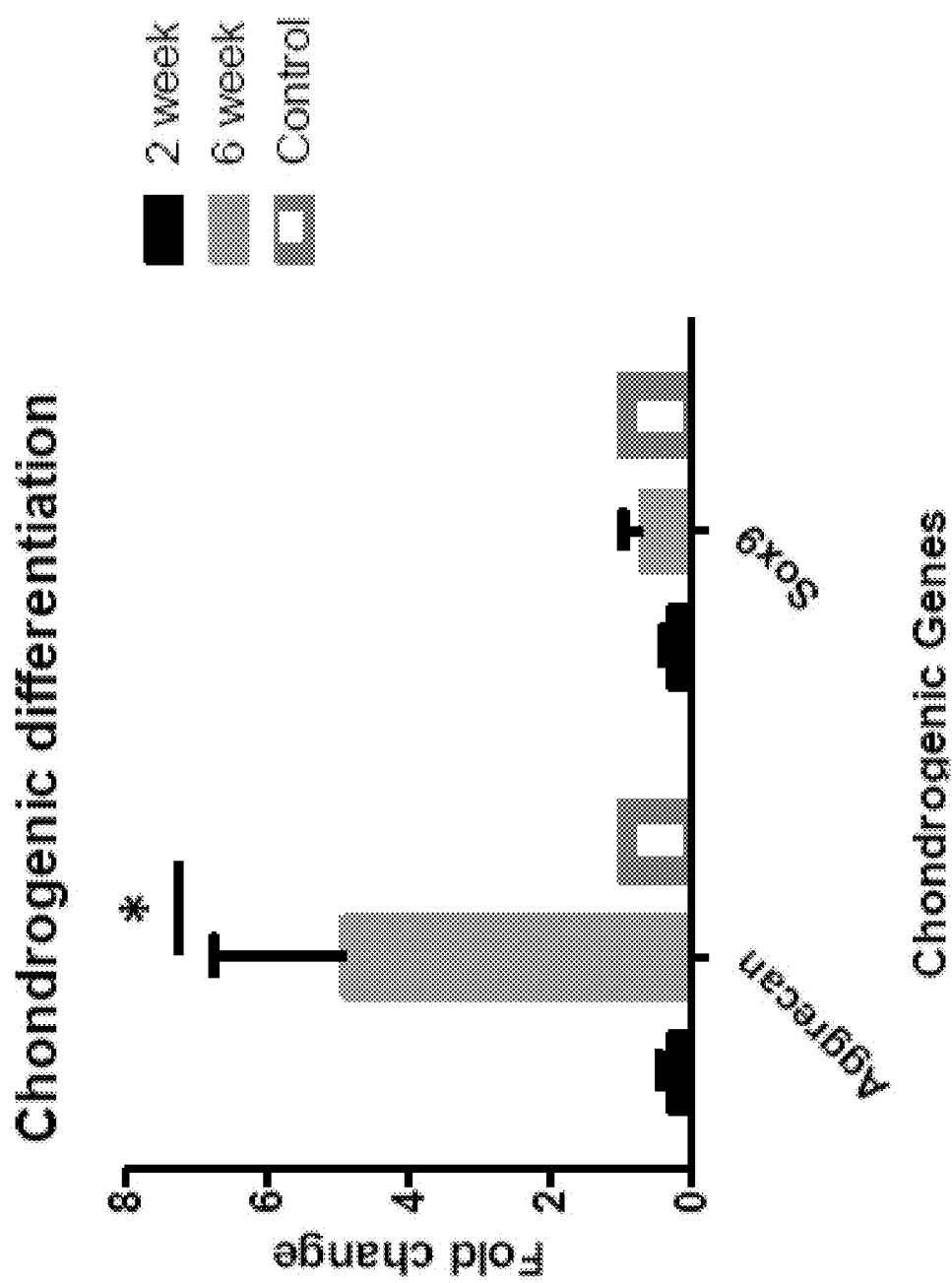
FIG. 18B includes a graph that shows chondrogenic differentiation for chondrogenic genes at 2 and 6 weeks.

We evaluated molecular tests supportive of osteogenic and chondrogenic differentiation at two time points: 2 and 6 weeks following induction of osteogenic or chondrogenic differentiation (see FIG. 18A). In these experiments, we did not appreciate significant increase in osteogenic or chondrogenic differentiation markers over controls after 2 weeks of osteogenic or chondrogenic induction (see FIG. 18A). FIG. 18A shows osteogenic gene expression (relative to 2 week and 6 week controls each normalized to 1) for type I collagen (COL I), runt-related transcription factor 2 (RUNX2), and osteocalcin (OCN) at week 2 (n=3) and week 6 (n=3). On the other hand, after 6 weeks of osteogenic differentiation, molecular markers of osteogenic differentiation (COLI, RUNX2, and OCN) all demonstrated significant increase over their respective week 6 control values (FIG. 18A). COL I and RUNX2 were expressed approximately 4 times their respective control values while OCN was expressed approximately 8 times its respective control value. On the other hand, aggrecan significantly increased over its respective week 6 control values after 6 weeks of chondrogenic differentiation (see FIG. 18B). FIG. 18B shows chondrogenic gene expression (relative to 2 week and 6 week controls each normalized to 1) for sex determining region Y-box 9 (SOX-9) and aggrecan. SOX-9 expression remained below control expression levels, while aggrecan expression was 4 times its respective control expression levels at 6 week time point, which was statistically significant. Collectively, these results indicate successful osteogenic and chondrogenic differentiation by WJMSCs seeded on DWJM scaffolds and induced to undergo osteogenic or chondrogenic differentiation.

Mechanical Testing

We tested stiffness, which is a measure of the resistance offered by an elastic body to deformation, as a mechanical property of the DWJM after osteogenic and chondrogenic differentiation. We noticed that all the tested material produced a curve characteristic of elastomeric scaffolds. DWJM after 4 weeks of chondrogenic differentiation, however, exhibited more stiffness than either DWJM or DWJM after 4 weeks of osteogenic differentiation, however, the difference was not statistically significant. On the other hand, the stiffness of DWJM after 4 weeks of osteogenic differentiation was significantly higher than DWJM prior to differentiation. We noticed that all the tested materials produced a curve characteristic of elastomeric scaffolds (data not shown). DWJM scaffolds after 4 weeks of chondrogenic differentiation or chondrogenic differentiation exhibited about 1.5× to 2× more stiffness than DWJM scaffolds prior to differentiation. A statistically significant difference in stiffness of osteogenic and chondrogenic DWJM scaffolds was demonstrated in comparison to original DWJM scaffolds. The difference in tissue stiffness of osteogenic differentiated and chondrogenic differentiated DWJM scaffolds was not significant.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

TABLE I

Proteins identified in the decellularized Wharton's jelly matrix

| Protein name | Accession number (1)* | Sequence coverage | MW [kDa] | Theoretical. pI | Peptides number | Number of Unique Peptides |
| --- | --- | --- | --- | --- | --- | --- |
| Collagen alpha-3(VI) | 219521324 | 13.70 | 278.0 | 8.15 | 18 | 18 |
| Collagen type I alpha-1 | 110349772 | 6.01 | 138.8 | 5.80 | 7 | 2 |
| Collagen type I alpha 1 | 180392 | 9.13 | 98.5 | 6.83 | 7 | 2 |
| Collagen, type VI, alpha 1 | 119629727 | 12.06 | 108.5 | 5.43 | 8 | 8 |
| Human Serum Albumin | 55669910 | 16.78 | 65.2 | 5.80 | 7 | 7 |
| Collagen type I alpha 2 | 825646 | 6.49 | 72.2 | 7.96 | 4 | 4 |
| Collagen type VI alpha-2 isoform 2C2 | 115527062 | 13.74 | 108.5 | 6.21 | 8 | 8 |
| Fibronectin 1 | 219518912 | 5.38 | 239.5 | 5.88 | 5 | 5 |
| G-gamma-hemoglobin | 183851 | 31.68 | 11.0 | 6.68 | 2 | 2 |
| Protein kinase, DNA-activated, catalytic polypeptide | 119607089 | 0.47 | 458.5 | 7.08 | 1 | 1 |
| Tenascin C | 156229767 | 4.93 | 210.4 | 4.98 | 4 | 4 |

TABLE I-continued

Proteins identified in the decellularized Wharton's jelly matrix

| Protein name | Accession number (1)* | Sequence coverage | MW [kDa] | Theoretical. pI | Peptides number | Number of Unique Peptides |
|---|---|---|---|---|---|---|
| TGFBI | 221044656 | 19.25 | 55.7 | 6.84 | 4 | 4 |
| Lumican | 4505047 | 15.68 | 38.4 | 6.61 | 3 | 3 |
| Collagen, type III, alpha 1 | 119631314 | 2.66 | 106.3 | 8.10 | 2 | 2 |
| Osteoglycin | 55957237 | 13.06 | 30.4 | 8.34 | 3 | 3 |
| TGFBI | 37589544 | 3.00 | 75.1 | 7.23 | 1 | 1 |
| Actin, alpha | 119612724 | 12.50 | 30.3 | 5.00 | 2 | 1 |
| Beta actin, gamma 1 | 194375299 | 10.21 | 37.3 | 5.71 | 2 | 1 |
| HCG2044004 | 119628289 | 46.88 | 3.6 | 9.32 | 1 | 1 |
| Collagen, type XII, alpha 1, isoform CRA_c | 119569135 | 2.22 | 333.0 | 5.53 | 3 | 3 |
| Hemoglobin alpha 2 | 13958153 | 59.21 | 8.4 | 7.14 | 2 | 2 |
| Immunoglobulin heavy chain variable region | 145911949 | 33.33 | 9.6 | 6.52 | 1 | 1 |
| Ig G1 H Nie | 229601 | 3.57 | 49.2 | 8.54 | 1 | 1 |
| Decorin | 119617856 | 14.29 | 28.0 | 8.13 | 2 | 2 |
| Unnamed protein product | 40036688 | 17.72 | 17.8 | 8.38 | 1 | 1 |
| N6AMT2 | 119628685 | 29.07 | 9.8 | 4.36 | 1 | 1 |
| Dynein, axonemal, heavy chain 14 | 220732359 | 5.31 | 40.7 | 5.21 | 1 | 1 |
| Chain D, Crystal Structure Of A Spare-Collagen Complex | 215261061 | 36.36 | 3.0 | 11.00 | 1 | 1 |
| Golgin subfamily A member 3 (GOLGA3) protein | 38174254 | 4.63 | 93.0 | 5.05 | 1 | 1 |
| Glyceraldehyde 3-phosphate dehydrogenase | 134254708 | 14.46 | 17.3 | 8.60 | 1 | 1 |
| Triacylglycerol lipase (EC 3.1.1.3), hormone-sensitive - human | 1082874 | 3.18 | 85.4 | 7.77 | 1 | 1 |
| PLEKHG3 protein | 120537866 | 3.32 | 80.8 | 5.40 | 1 | 1 |
| OPK V NimA family | 38502049 | 4.01 | 67.9 | 8.98 | 1 | 1 |
| Plexin D1, isoform CRA_c | 119599646 | 1.09 | 193.4 | 6.96 | 1 | 1 |
| CDH24 | 28375477 | 10.79 | 26.3 | 5.43 | 1 | 1 |
| Beta IV spectrin isoform sigma3 | 11602888 | 1.76 | 148.5 | 6.37 | 1 | 1 |
| FBLN1 | 22761800 | 3.61 | 70.5 | 5.91 | 1 | 1 |
| Unnamed protein product | 40035675 | 3.16 | 68.9 | 9.32 | 1 | 1 |
| Immunoglobulin heavy chain variable region | 13171510 | 52.73 | 6.2 | 8.76 | 1 | 1 |
| Periostin isoform thy8 | 166343771 | 3.19 | 80.3 | 8.19 | 1 | 1 |
| Transferrin receptor protein 2 | 33589848 | 3.37 | 88.7 | 6.11 | 1 | 1 |
| H2AFJ | 194382012 | 17.12 | 12.1 | 10.40 | 1 | 1 |
| Large tumor suppressor, homolog 2 variant | 62089380 | 1.95 | 101.4 | 9.22 | 1 | 1 |
| Truncated beta-globin | 58201131 | 47.50 | 4.5 | 9.47 | 1 | 1 |
| Anti-vaccinia virus immunoglobulin light chain variable region | 316925527 | 19.44 | 11.4 | 7.12 | 1 | 1 |
| Carboxypeptidase A1 (pancreatic) | 30583465 | 4.30 | 47.1 | 5.77 | 1 | 1 |

Abbreviations: TGFBI: transforming growth factor, beta-induced, FBLN1: fibulin-1, H2AFJ: histone H2A.J.
*Accession number refers to the accession number in the National Center for Biotechnology Information (NCBI) protein database.

The invention claimed is:

1. A method for promoting hair growth comprising: (A) providing a tissue scaffold comprising CK19-positive cells in a decellularized Wharton's jelly matrix, wherein the CK19-positive cells are derived from Wharton's jelly mesenchymal stromal (WJMS) cells that have been seeded on the decellularized Wharton's jelly matrix and then incubated in an osteogenic differentiation media; and (B) implanting the tissue scaffold into a skin surface of a subject such that implantation of the tissue scaffold promotes hair growth at or close to the surface of the skin.

2. The method of claim 1 wherein the tissue scaffold is implanted into a scalp of the subject.

3. The method of claim 1 wherein one or more of versican, sonic hedgehog, and bone morphogenic protein-4 (BMP-4) is detected in a region in the tissue scaffold.

4. The method of claim 3 wherein the tissue scaffold comprises CK19-positive cells that have differentiated into condensed cells or are in the process of differentiating into condensed cells and wherein one or more layers of spindle-like cells overlay the area of condensed cells.

5. The method of claim 4 wherein the tissue scaffold comprises a placode.

6. The method of claim 1 wherein prior to (A), providing the WJMS cells; seeding the WJMS cells on the tissue scaffold comprising decellularized Wharton's jelly matrix; and incubating the tissue scaffold comprising the decellularized Wharton's jelly matrix seeded with WJMS cells in the osteogenic differentiation media until the WJMS cells seeded on the decellularized Wharton's jelly matrix differentiate into CK19-positive cells.

7. The method of claim 1 wherein the tissue scaffold comprises one or more of: mesenchymal cell condensation, hair placode formation, spindle-like cell layer, and hair follicle formation.

8. The method of claim 5 wherein the tissue scaffold is implanted into a scalp of a subject.

9. The method of claim 1 wherein prior to (A), providing the tissue scaffold comprising decellularized Wharton's jelly matrix; seeding WJMS cells on the tissue scaffold comprising decellularized Wharton's jelly matrix; incubating the tissue scaffold comprising the decellularized Wharton's jelly matrix seeded with WJMS cells in a cell growth media; and incubating the tissue scaffold comprising the decellularized Wharton's jelly matrix seeded with WJMS cells in the osteogenic differentiation media until the WJMS cells differentiate into CK19-positive cells.

10. The method of claim 9 wherein prior to providing the tissue scaffold comprising decellularized Wharton's jelly matrix, the Wharton's jelly matrix is decellularized and the decellularization process removes all cells and cellular elements from the Wharton's jelly matrix.

11. The method of claim 9, wherein the cell growth media excludes: dexamethasone, β-glycerophosphate, 1α, 25-hydroxyvitamin D3, and ascorbic acid 2-phosphate.

12. The method of claim 1 wherein the matrix has interstitial spaces.

13. The method of claim 9 wherein the seeded WJMS cells are incubated in the tissue scaffold comprising decellularized Wharton's jelly matrix in the osteogenic differentiation media until one or more of versican, sonic hedgehog, and bone morphogenic protein-4 (BMP-4) is detected in a region in the tissue scaffold.

14. The method of claim 12 wherein the seeded WJMS cells are incubated in the tissue scaffold comprising decellularized Wharton's jelly matrix in the osteogenic differentiation media until an area of condensed cells forms with one or more layers of spindle-like cells over the area of condensed cells.

15. The method of claim 14 wherein the seeded WJMS cells are incubated in the tissue scaffold comprising decellularized Wharton's jelly matrix in the osteogenic differentiation media until a placode is formed.

16. The method of claim 15 wherein the seeded WJMS cells are incubated in the tissue scaffold comprising decellularized Wharton's jelly matrix in the osteogenic differentiation media until a hair follicle-like structure is formed.

17. The method of claim 15 wherein the seeded WJMS cells are incubated in the tissue scaffold comprising decellularized Wharton's jelly matrix in the osteogenic differentiation media until an osteogenic portion is obtained.

18. The method of claim 1 wherein prior to (A) providing the tissue scaffold comprising decellularized Wharton's jelly matrix; seeding WJMS cells on the tissue scaffold comprising decellularized Wharton's' jelly matrix; incubating the tissue scaffold comprising the decellularized Wharton's jelly matrix seeded with WJMS cells in an expansion media; and incubating the tissue scaffold comprising the decellularized Wharton's jelly matrix seeded with WJMS cells in the osteogenic differentiation media until spheroids comprising the CK19-positive cells are obtained.

19. The method of claim 18 wherein prior to (A) providing the tissue scaffold comprising decellularized Wharton's jelly matrix; seeding WJMS cells on the tissue scaffold comprising decellularized Wharton's jelly matrix; incubating the tissue scaffold comprising the decellularized Wharton's jelly matrix seeded with WJMS cells in the osteogenic media until one or more of (1) one or more of versican, sonic hedgehog, and bone morphogenic protein-4 (BMP-4) is detected in a region in the tissue scaffold; (2) an area of condensed cells forms with one or more layers of spindle-like cells over the area of condensed cells; (3) a placode is formed and (4) a hair follicle-like structure is formed.

* * * * *